United States Patent
Ross et al.

(10) Patent No.: US 10,485,864 B2
(45) Date of Patent: Nov. 26, 2019

(54) CHARACTERIZATION OF INFLUENZA VACCINES

(71) Applicant: OREGON HEALTH & SCIENCE UNIVERSITY, Portland, OR (US)

(72) Inventors: Ted Milburn Ross, Watkinsville, GA (US); Terianne Maiko Wong, Athens, GA (US); Donald Martin Carter, Jr., Athens, GA (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 15/762,050

(22) PCT Filed: Sep. 21, 2016

(86) PCT No.: PCT/US2016/052802
§ 371 (c)(1),
(2) Date: Mar. 21, 2018

(87) PCT Pub. No.: WO2017/053374
PCT Pub. Date: Mar. 30, 2017

(65) Prior Publication Data
US 2018/0271972 A1 Sep. 27, 2018

Related U.S. Application Data

(60) Provisional application No. 62/221,336, filed on Sep. 21, 2015.

(51) Int. Cl.
| | | |
|---|---|---|
| *A61K 39/145* | (2006.01) | |
| *A61K 39/39* | (2006.01) | |
| *C07K 14/005* | (2006.01) | |
| *C12N 9/24* | (2006.01) | |
| *A61P 31/16* | (2006.01) | |
| *A61K 9/00* | (2006.01) | |
| *C07K 14/11* | (2006.01) | |
| *C12N 15/63* | (2006.01) | |
| *A61K 39/00* | (2006.01) | |

(52) U.S. Cl.
CPC .......... *A61K 39/145* (2013.01); *A61K 9/0019* (2013.01); *A61K 39/39* (2013.01); *A61P 31/16* (2018.01); *C07K 14/005* (2013.01); *C07K 14/11* (2013.01); *C12N 9/24* (2013.01); *C12N 15/63* (2013.01); *A61K 2039/5258* (2013.01); *C12N 2740/16222* (2013.01); *C12N 2760/16123* (2013.01); *C12N 2760/16134* (2013.01); *C12N 2760/16171* (2013.01); *C12Y 302/01* (2013.01)

(58) Field of Classification Search
CPC .............. C07K 14/005; C07K 16/1018; C07K 2317/32; C07K 2317/34; C07K 14/11; C07K 2317/33; C12Q 2600/136; C12Q 2600/156; G01N 2333/11; G01N 33/56983; G01N 25/00; B82Y 5/00; A61K 39/145; A61K 2039/5258; A61K 9/0019; A61K 39/39; A61K 39/12; A61P 31/16; C12Y 302/01; C12N 2740/16222; C12N 2760/16171; C12N 2760/16134; C12N 2760/16123; C12N 15/63; C12N 9/24
See application file for complete search history.

(56) References Cited

U.S. PATENT DOCUMENTS

| | | | |
|---|---|---|---|
| 2010/0028375 A1* | 2/2010 | Lua ...................... | A61K 39/145 424/186.1 |
| 2013/0183342 A1* | 7/2013 | Ross ...................... | C07K 14/11 424/210.1 |
| 2015/0030628 A1 | 1/2015 | Ross et al. | |
| 2015/0044247 A1 | 2/2015 | Ross et al. | |

FOREIGN PATENT DOCUMENTS

| | | | |
|---|---|---|---|
| JP | 5735121 | 6/2015 | |
| WO | 2012036993 | 3/2012 | |
| WO | 2012/088428 | 6/2012 | |
| WO | WO-2013119683 A1 * | 8/2013 | ........... A61K 39/145 |

OTHER PUBLICATIONS

Wasik MA, Eichwald L, Genzel Y, Reichl U. Cell culture-based production of defective interfering particles for influenza antiviral therapy. Appl Microbiol Biotechnol. Feb. 2018;102(3):1167-1177. Epub Dec. 5, 2017.*
Spiro D, et. al. Hemagglutinin. GenBank Acc. No. ABG88817.1. Dep. Sep. 5, 2006.*
Ghedin E et. al. Hemagglutinin [Influenza A virus (A/Hong Kong/14/1974(H3N2))]. GenBank: ABB04294.1. Dep. Apr. 4, 2014.*
PCT/US2016/052802, "International Preliminary Report on Patentability", dated Apr. 5, 2018, 12 pages.
"NCBI", GenBank accession No. ABD62843.1, Oct. 24, 2007.
PCT/US2016/052802, "International Search Report and Written Opinion", dated Dec. 30, 2016, 17 pages.
Database Uniparc [Online], "Influenza A virus (A/Alborz/1095/2012 (H3N2))", XP002789958, retrieved from UniProt Database accession No. UPI00032B3BE9, Jun. 26, 2013.
Database Uniparc [Online], "Influenza A virus (A/Guildford/V728/1985 (H3N2))", XP002789954, retrieved from UniProt Database accession No. UPI000256DCD9, Jun. 13, 2012.
Database Uniparc [Online], "Influenza A virus (A/Hong Kong/14/1974 (H3N2))", XP002789952, retrieved from UniProt Database accession No. UPI00005CE2E5, Nov. 22, 2005.

(Continued)

*Primary Examiner* — Rachel B Gill
(74) *Attorney, Agent, or Firm* — Kilpatrick Townsend & Stockton LLP

(57) ABSTRACT

Provided herein are optimized, recombinant influenza HA polypeptides that elicit immune responses. Also provided are compositions and kits comprising the optimized HA polypeptides as well as methods of making and using the optimized HA polypeptides.

15 Claims, 3 Drawing Sheets

Specification includes a Sequence Listing.

(56) References Cited

OTHER PUBLICATIONS

Database Uniparc [Online], "Influenza A virus (A/Mexico/DIF2601/2005 (H3N2))", XP002789960, retrieved from UniProt Database accession No. UPI00049A8486, Sep. 3, 2014.

Database Uniparc [Online], "Influenza A virus (A/Netherlands/620/1989 (H3N2))", XP002789955, retrieved from UniProt Database accession No. UPI000256DE5E, Jun. 13, 2012.

Database Uniparc [Online], "Influenza A virus (A/New South Wales/17/1999 (H3N2))", XP002789961, retrieved from UniProt Database accession No. UPI0000E455D0, Nov. 14, 2006.

Database Uniparc [Online], "Influenza A virus (A/New York/1021/2006 (H3N2))", XP002789959, retrieved from UniProt Database accession No. UPI000442A752, Jun. 11, 2014.

Database Uniparc [Online], "Influenza A virus (A/New York/773/1993 (H3N2))", XP002789956, retrieve from UniProt Database accession No. UPI0000DB3CB2, Sep. 19, 2006.

Database Uniparc [Online], "Influenza A virus (A/Perth/49/2010 (H3N2))", XP002789957, retrieved from UniProt Database accession No. UPI0002117247, Sep. 16, 2015.

Database Uniparc [Online], "Influenza A virus (A/Netherlands/233/1982 (H3N2))", XP002789953, retrieved from UniProt Database accession No. UPI00052A2FE8, Jan. 7, 2015.

Deo et al., "Chimeric Virus-Like Particles Made Using GAG and M1 Capsid Proteins Providing Dual Drug Delivery and Vaccination Platform", Molecular Pharmaceutics, vol. 12, No. 3, XP055572632, Mar. 2, 2015, 839-845.

EP16849471.4, "Extended European Search Report", dated Apr. 17, 2019, 12 pages.

Houser et al., "Influenza Vaccines: Challenges and Solutions", Cell Host & Microbe, vol. 17, No. 3, XP055572607, Mar. 1, 2015, 295-300.

* cited by examiner

| | 15-virus DRIFT PANEL | Fuji/02 | Wis/05 | Bris/07 | Perth/09 | T-6 | T-7 | T-8 | T-10 | T-11 |
|---|---|---|---|---|---|---|---|---|---|---|
| | A/New York/55/2004 | 40 | 80 | 10 | 40 | 10 | 320 | 80 | 10 | 320 |
| Variant to 2006 vaccine | A/Hong Kong/CUHK53726/2004 | 10 | 40 | 10 | 10 | 10 | 160 | 10 | 10 | 160 |
| A/Wisconsin/67/2005 | A/Wisconsin/67/2005 | 20 | 320 | 40 | 640 | 10 | 1280 | 2560 | 80 | 1280 |
| | A/Florida/2/2006 | 10 | 80 | 20 | 160 | 10 | 640 | 1280 | 10 | 640 |
| * | A/Santiago/7981/2006 | 10 | 20 | 40 | 10 | 10 | 320 | 320 | 10 | 320 |
| * | A/Lyon/636/2006 | 10 | 20 | 10 | 10 | 10 | 160 | 10 | 10 | 160 |
| * | A/Malaysia/1674395/2006 | 10 | 20 | 10 | 160 | 10 | 320 | 640 | 10 | 320 |
| * | A/Nepal/921/2006 | 10 | 40 | 20 | 160 | 10 | 320 | 640 | 20 | 320 |
| * | A/Trieste/25/2007 | 10 | 40 | 10 | 80 | 10 | 640 | 640 | 20 | 320 |
| | A/Brisbane/10/2007 | | | | | | | | | |
| * | A/Thailand/359/2007 | 10 | 40 | 10 | 160 | 10 | 320 | 640 | 20 | 320 |
| * | A/Henan/Jinshui/147/2007 | 10 | 40 | 40 | 10 | 10 | 320 | 320 | 10 | 320 |
| * | A/Uruguay/716/2007 | 10 | 40 | 80 | 20 | 10 | 640 | 320 | 10 | 640 |
| * | A/Texas/71/2007 | 10 | 20 | 10 | 20 | 10 | 160 | 160 | 10 | 160 |
| * | A/Taiwan/760/2007 | 10 | 40 | 10 | 20 | 10 | 320 | 160 | 10 | 320 |
| * | A/Perth/16/2009 | 10 | 10 | 10 | 5120 | 10 | 40 | 160 | 640 | 1280 |
| *=8-fold reduction | # of viruses >40 (15 total) | 1 | 10 | 4 | 8 | 0 | 15 | 13 | 2 | 15 |
| *=16-fold reduction | # of viruses >80 (15 total) | 0 | 3 | 1 | 7 | 0 | 14 | 13 | 2 | 15 |

SEQUENCE LISTING

```
<160> NUMBER OF SEQ ID NOS: 30

<210> SEQ ID NO 1
<211> LENGTH: 566
<212> TYPE: PRT
<213> ORGANISM: Artificial Sequence
<220> FEATURE:
<223> OTHER INFORMATION: Synthetic Construct

<400> SEQUENCE: 1
```

```
Met Lys Thr Ile Ile Ala Leu Ser Tyr Ile Phe Cys Leu Val Leu Gly
1               5                   10                  15

Gln Asp Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Ser Ser Thr
50                      55                  60

Gly Lys Ile Cys Asn Asn Pro His Arg Ile Leu Asp Gly Ile Asn Cys
65                      70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Asn Glu Gly Phe Asn Trp Thr
130                 135                 140

Gly Val Thr Gln Asn Gly Gly Ser Asn Ala Cys Lys Arg Gly Pro Asp
145                 150                 155                 160

Ser Gly Phe Phe Ser Arg Leu Asn Trp Leu Tyr Lys Ser Gly Ser Thr
                165                 170                 175

Tyr Pro Val Leu Asn Val Thr Met Pro Asn Asn Asp Asn Phe Asp Lys
                180                 185                 190

Leu Tyr Ile Trp Gly Val His His Pro Ser Thr Asp Gln Glu Gln Thr
            195                 200                 205

Ser Leu Tyr Val Gln Ala Ser Gly Arg Val Thr Val Ser Thr Lys Arg
210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Gly Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Ile Asp Gly Trp Tyr Gly
            355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415
```

-continued

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 2
<211> LENGTH: 567
<212> TYPE: PRT
<213> ORGANISM: Artificial Sequence
<220> FEATURE:
<223> OTHER INFORMATION: Synthetic Construct

<400> SEQUENCE: 2

Met Lys Thr Ile Ile Ala Leu Ser Tyr Ile Phe Cys Leu Val Phe Ala
1               5                   10                  15

Gln Asn Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Asn Glu Gly Phe Asn Trp Thr
        130                 135                 140

Gly Val Thr Gln Ser Gly Gly Ser Tyr Ala Cys Lys Arg Gly Ser Asp
145                 150                 155                 160

Asn Ser Phe Phe Ser Arg Leu Asn Trp Leu Tyr Glu Ser Glu Ser Lys
                165                 170                 175

Tyr Pro Ala Leu Asn Val Thr Met Pro Asn Asn Gly Asn Phe Asp Lys
            180                 185                 190

Leu Tyr Ile Trp Gly Val His His Pro Ser Thr Asp Lys Glu Gln Thr
        195                 200                 205

```
Asn Leu Tyr Val Arg Ala Ser Gly Arg Val Thr Val Ser Thr Lys Arg
    210                 215                 220
Ser Gln Gln Thr Val Ile Pro Asn Ile Gly Ser Arg Pro Trp Val Arg
225                 230                 235                 240
Gly Leu Ser Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Thr Gly Lys Ser Ser Ile Met Arg Ser Asp Ala
        275                 280                 285
Pro Ile Gly Thr Cys Ser Ser Glu Cys Ile Thr Pro Asn Gly Ser Ile
    290                 295                 300
Pro Asn Asp Lys Pro Phe Gln Asn Val Asn Lys Ile Thr Tyr Gly Ala
305                 310                 315                 320
Cys Pro Lys Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Thr Gly Gln Ala Ala Asp Leu Lys
    370                 375                 380
Ser Thr Gln Ala Ala Ile Asp Gln Ile Asn Gly Lys Leu Asn Arg Leu
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Lys Thr Arg Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Val Leu Leu Gly Phe Ile Met Trp Ala Cys Gln Lys Gly Asn Ile
545                 550                 555                 560
Arg Cys Asn Ile Cys Ile Thr
                565

<210> SEQ ID NO 3
<211> LENGTH: 566
<212> TYPE: PRT
<213> ORGANISM: Artificial Sequence
<220> FEATURE:
<223> OTHER INFORMATION: Synthetic Construct

<400> SEQUENCE: 3
```

```
Met Lys Thr Ile Ile Ala Leu Ser Tyr Ile Phe Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Gly Phe Asn Trp Thr
130                 135                 140

Gly Val Thr Gln Ser Gly Gly Ser Tyr Ala Cys Lys Arg Gly Ser Val
145                 150                 155                 160

Asn Ser Phe Phe Ser Arg Leu Asn Trp Leu Tyr Lys Ser Glu Ser Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Lys Glu Gln Thr
        195                 200                 205

Asn Leu Tyr Val Arg Ala Ser Gly Arg Val Thr Val Ser Thr Lys Arg
210                 215                 220

Ser Gln Gln Thr Val Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
```

```
                420             425             430
Lys Ile Asp Leu Trp Ser Tyr Asn Ala Glu Leu Leu Val Ala Leu Glu
            435             440             445

Asn Gln His Thr Ile Asp Leu Thr Asp Ser Glu Met Asn Lys Leu Phe
        450             455             460

Glu Lys Thr Arg Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
                485             490             495

Ile Arg Asn Gly Thr Tyr Asp His Asp Val Tyr Arg Asp Glu Ala Leu
            500             505             510

Asn Asn Arg Phe Gln Ile Lys Gly Val Glu Leu Lys Ser Gly Tyr Lys
        515             520             525

Asp Trp Ile Leu Trp Ile Ser Phe Ala Ile Ser Cys Phe Leu Leu Cys
    530             535             540

Val Val Leu Leu Gly Phe Ile Met Trp Ala Cys Gln Lys Gly Asn Ile
545             550             555             560

Arg Cys Asn Ile Cys Ile
                565

<210> SEQ ID NO 4
<211> LENGTH: 566
<212> TYPE: PRT
<213> ORGANISM: Artificial Sequence
<220> FEATURE:
<223> OTHER INFORMATION: Synthetic Construct

<400> SEQUENCE: 4

Met Lys Thr Ile Ile Ala Leu Ser Tyr Ile Phe Cys Leu Val Phe Ala
1               5              10              15

Gln Lys Leu Pro Gly Asn Asp Asn Ser Thr Ala Thr Leu Cys Leu Gly
            20              25              30

His His Ala Val Pro Asn Gly Thr Leu Val Lys Thr Ile Thr Asn Asp
        35              40              45

Gln Ile Glu Val Thr Asn Ala Thr Glu Leu Val Gln Ser Ser Ser Thr
    50              55              60

Gly Arg Ile Cys Asp Ser Pro His Arg Ile Leu Asp Gly Lys Asn Cys
65              70              75              80

Thr Leu Ile Asp Ala Leu Leu Gly Asp Pro His Cys Asp Gly Phe Gln
                85              90              95

Asn Glu Glu Trp Asp Leu Phe Val Glu Arg Ser Lys Ala Tyr Ser Asn
            100             105             110

Cys Tyr Pro Tyr Asp Val Pro Asp Tyr Ala Ser Leu Arg Ser Leu Val
        115             120             125

Ala Ser Ser Gly Thr Leu Glu Phe Ile Asn Glu Asp Phe Asn Trp Thr
    130             135             140

Gly Val Ala Gln Ser Gly Gly Ser Tyr Ala Cys Lys Arg Gly Ser Val
145             150             155             160

Asn Ser Phe Phe Ser Arg Leu Asn Trp Leu His Glu Ser Glu Tyr Lys
                165             170             175

Tyr Pro Ala Leu Asn Val Thr Met Pro Asn Asn Gly Lys Phe Asp Lys
            180             185             190

Leu Tyr Ile Trp Gly Val His His Pro Ser Thr Asp Arg Glu Gln Thr
        195             200             205

Asn Leu Tyr Val Arg Ala Ser Gly Arg Val Thr Val Ser Thr Lys Arg
```

```
Ser Gln Gln Thr Val Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
                260                 265                 270

Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 5
<211> LENGTH: 566
<212> TYPE: PRT
<213> ORGANISM: Artificial Sequence
<220> FEATURE:
<223> OTHER INFORMATION: Synthetic Construct

<400> SEQUENCE: 5

Met Lys Thr Ile Ile Ala Leu Ser Tyr Ile Leu Cys Leu Val Phe Ala
```

-continued

```
1               5               10              15
Gln Lys Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
                35                  40                  45

Gln Ile Glu Val Thr Asn Ala Thr Glu Leu Val Gln Ser Ser Ser Thr
 50                  55                  60

Gly Arg Ile Cys Asp Ser Pro His Arg Ile Leu Asp Gly Lys Asn Cys
 65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
                115                 120                 125

Ala Ser Ser Gly Thr Leu Glu Phe Ile Asn Glu Asp Phe Asn Trp Thr
 130                 135                 140

Gly Val Ala Gln Asp Gly Lys Ser Tyr Ala Cys Lys Arg Gly Ser Val
 145                 150                 155                 160

Asn Ser Phe Phe Ser Arg Leu Asn Trp Leu His Lys Leu Glu Tyr Lys
                165                 170                 175

Tyr Pro Ala Leu Asn Val Thr Met Pro Asn Asn Asp Lys Phe Asp Lys
                180                 185                 190

Leu Tyr Ile Trp Gly Val His His Pro Ser Thr Asp Ser Asp Gln Thr
                195                 200                 205

Ser Leu Tyr Val Gln Ala Ser Gly Arg Val Thr Val Ser Thr Lys Arg
 210                 215                 220

Ser Gln Gln Thr Val Ile Pro Asn Ile Gly Ser Arg Pro Trp Val Arg
 225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Asn Gly Lys Ser Ser Ile Met Arg Ser Asp Ala
                275                 280                 285

Pro Ile Gly Asn Cys Asn Ser Glu Cys Ile Thr Pro Asn Gly Ser Ile
                290                 295                 300

Pro Asn Asp Lys Pro Phe Gln Asn Val Asn Arg Ile Thr Tyr Gly Ala
 305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Thr Gly Gln Ala Ala Asp Leu Lys
                370                 375                 380

Ser Thr Gln Ala Ala Ile Asp Gln Ile Asn Gly Lys Leu Asn Arg Leu
 385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430
```

```
Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
    450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 6
<211> LENGTH: 566
<212> TYPE: PRT
<213> ORGANISM: Artificial Sequence
<220> FEATURE:
<223> OTHER INFORMATION: Synthetic Construct

<400> SEQUENCE: 6

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Arg Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
130                 135                 140

Gly Val Ala Gln Asn Gly Thr Ser Ser Ala Cys Lys Arg Arg Ser Ile
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Ser Thr Asp Ser Asp Gln Ile
        195                 200                 205

Ser Leu Tyr Ala Gln Ala Ser Gly Arg Val Thr Val Ser Thr Lys Arg
    210                 215                 220
```

Ser Gln Gln Thr Val Ile Pro Asn Ile Gly Ser Arg Pro Trp Val Arg
225                 230                 235                 240

Gly Val Ser Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 7
<211> LENGTH: 566
<212> TYPE: PRT
<213> ORGANISM: Artificial Sequence
<220> FEATURE:
<223> OTHER INFORMATION: Synthetic Construct

<400> SEQUENCE: 7

Met Lys Thr Ile Ile Ala Leu Ser Tyr Ile Leu Cys Leu Val Phe Ala
1               5                   10                  15

```
Gln Lys Leu Pro Gly Asn Asp Asn Ser Thr Ala Thr Leu Cys Leu Gly
             20                  25                  30

His His Ala Val Pro Asn Gly Thr Ile Val Lys Thr Ile Thr Asn Asp
         35                  40                  45

Gln Ile Glu Val Thr Asn Ala Thr Glu Leu Val Gln Ser Ser Ser Thr
 50                  55                  60

Gly Glu Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
                 100                 105                 110

Cys Tyr Pro Tyr Asp Val Pro Asp Tyr Ala Ser Leu Arg Ser Leu Val
             115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                 165                 170                 175

Tyr Pro Ala Leu Asn Val Thr Met Pro Asn Asn Glu Lys Phe Asp Lys
             180                 185                 190

Leu Tyr Ile Trp Gly Val His His Pro Gly Thr Asp Asn Asp Gln Ile
             195                 200                 205

Phe Leu Tyr Ala Gln Ala Ser Gly Arg Ile Thr Val Ser Thr Lys Arg
             210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                 245                 250                 255

Asp Ile Leu Leu Ile Asn Ser Thr Gly Asn Leu Ile Ala Pro Arg Gly
                 260                 265                 270

Tyr Phe Lys Ile Arg Ser Gly Lys Ser Ser Ile Met Arg Ser Asp Ala
                 275                 280                 285

Pro Ile Gly Lys Cys Asn Ser Glu Cys Ile Thr Pro Asn Gly Ser Ile
             290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                 325                 330                 335

Arg Asn Val Pro Glu Lys Gln Thr Arg Gly Ile Phe Gly Ala Ile Ala
                 340                 345                 350

Gly Phe Ile Glu Asn Gly Trp Glu Gly Met Val Asp Gly Trp Tyr Gly
                 355                 360                 365

Phe Arg His Gln Asn Ser Glu Gly Ile Gly Gln Ala Ala Asp Leu Lys
             370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                 405                 410                 415

Glu Val Glu Gly Arg Ile Gln Asp Leu Glu Lys Tyr Val Glu Asp Thr
             420                 425                 430
```

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 8
<211> LENGTH: 566
<212> TYPE: PRT
<213> ORGANISM: Artificial Sequence
<220> FEATURE:
<223> OTHER INFORMATION: Synthetic Construct

<400> SEQUENCE: 8

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 9
<211> LENGTH: 566
<212> TYPE: PRT
<213> ORGANISM: Artificial Sequence
<220> FEATURE:
<223> OTHER INFORMATION: Synthetic Construct

<400> SEQUENCE: 9

Met Lys Thr Ile Ile Ala Leu Ser Tyr Ile Leu Cys Leu Val Phe Ala
1               5                   10                  15

-continued

```
Gln Lys Leu Pro Gly Asn Asp Asn Ser Thr Ala Thr Leu Cys Leu Gly
             20                  25                  30

His His Ala Val Pro Asn Gly Thr Ile Val Lys Thr Ile Thr Asn Asp
         35                  40                  45

Gln Ile Glu Val Thr Asn Ala Thr Glu Leu Val Gln Ser Ser Ser Thr
     50                  55                  60

Gly Arg Ile Cys Asp Ser Pro His Gln Ile Leu Asp Gly Glu Asn Cys
 65                  70                  75                  80

Thr Leu Ile Asp Ala Leu Leu Gly Asp Pro His Cys Asp Gly Phe Gln
                 85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Ser Phe Asn Trp Thr
    130                 135                 140

Gly Val Thr Gln Asn Gly Gly Ser Ser Ala Cys Lys Arg Gly Ser Asn
145                 150                 155                 160

Asn Ser Phe Phe Ser Arg Leu Asn Trp Leu Thr His Leu Glu Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Lys Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
```

```
                435             440             445
Asn Gln His Thr Ile Asp Leu Thr Asp Ser Glu Met Asn Lys Leu Phe
        450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 10
<211> LENGTH: 566
<212> TYPE: PRT
<213> ORGANISM: Artificial Sequence
<220> FEATURE:
<223> OTHER INFORMATION: Synthetic Construct

<400> SEQUENCE: 10

Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
                20                  25                  30
His His Ala Val Pro Asn Gly Thr Ile Val Lys Thr Ile Thr Asn Asp
            35                  40                  45
Gln Ile Glu Val Thr Asn Ala Thr Glu Leu Val Gln Ser Ser Ser Thr
        50                  55                  60
Gly Glu Ile Cys Asp Ser Pro His Gln Ile Leu Asp Gly Glu Asn Cys
65                  70                  75                  80
Thr Leu Ile Asp Ala Leu Leu Gly Asp Pro Gln Cys Asp Gly Phe Gln
                85                  90                  95
Asn Lys Lys Trp Asp Leu Phe Val Glu Arg Ser Lys Ala Tyr Ser Asn
                100                 105                 110
Cys Tyr Pro Tyr Asp Val Pro Asp Tyr Ala Ser Leu Arg Ser Leu Val
            115                 120                 125
Ala Ser Ser Gly Thr Leu Glu Phe Asn Asn Glu Ser Phe Asn Trp Thr
        130                 135                 140
Gly Val Thr Gln Asn Gly Thr Ser Ser Ala Cys Ile Arg Arg Ser Asn
145                 150                 155                 160
Asn Ser Phe Phe Ser Arg Leu Asn Trp Leu Thr His Leu Asn Phe Lys
                165                 170                 175
Tyr Pro Ala Leu Asn Val Thr Met Pro Asn Asn Glu Gln Phe Asp Lys
            180                 185                 190
Leu Tyr Ile Trp Gly Val His His Pro Gly Thr Asp Lys Asp Gln Ile
        195                 200                 205
Phe Leu Tyr Ala Gln Ala Ser Gly Arg Ile Thr Val Ser Thr Lys Arg
    210                 215                 220
Ser Gln Gln Thr Val Ile Pro Asn Ile Gly Ser Arg Pro Arg Val Arg
```

```
            225                 230                 235                 240

Asn Ile Pro Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
            290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                    325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Arg Gly Gln Ala Ala Asp Leu Lys
            370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                    405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                    485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 11
<211> LENGTH: 566
<212> TYPE: PRT
<213> ORGANISM: Artificial Sequence
<220> FEATURE:
<223> OTHER INFORMATION: Synthetic Construct

<400> SEQUENCE: 11

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
```

-continued

```
             20                  25                  30
His His Ala Val Pro Asn Gly Thr Ile Val Lys Thr Ile Thr Asn Asp
         35                  40                  45

Gln Ile Glu Val Thr Asn Ala Thr Glu Leu Val Gln Ser Ser Ser Thr
 50                  55                  60

Gly Glu Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
                115                 120                 125

Ala Ser Ser Gly Thr Leu Glu Phe Asn Asn Glu Ser Phe Asn Trp Thr
        130                 135                 140

Gly Val Thr Gln Asn Gly Thr Ser Ser Ala Cys Ile Arg Gly Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
                180                 185                 190

Leu Tyr Ile Trp Gly Val His His Pro Gly Thr Asp Lys Asp Gln Ile
                195                 200                 205

Phe Leu Tyr Ala Gln Ala Ser Gly Arg Ile Thr Val Ser Thr Lys Arg
        210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
        290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Arg Gly Gln Ala Ala Asp Leu Lys
                370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445
```

```
Asn Gln His Thr Ile Asp Leu Thr Asp Ser Glu Met Asn Lys Leu Phe
            450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
                500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 12
<211> LENGTH: 566
<212> TYPE: PRT
<213> ORGANISM: Artificial Sequence
<220> FEATURE:
<223> OTHER INFORMATION: Synthetic Construct

<400> SEQUENCE: 12

Met Lys Thr Ile Ile Ala Leu Ser Tyr Ile Cys Leu Val Phe Ala
1               5                   10                  15
Gln Lys Leu Pro Gly Asn Asp Asn Ser Thr Ala Thr Leu Cys Leu Gly
                20                  25                  30
His His Ala Val Pro Asn Gly Thr Leu Val Lys Thr Ile Thr Asn Asp
            35                  40                  45
Gln Ile Glu Val Thr Asn Ala Thr Glu Leu Val Gln Ser Ser Ser Thr
        50                  55                  60
Gly Arg Ile Cys Asp Ser Pro His Arg Ile Leu Asp Gly Glu Asn Cys
65                  70                  75                  80
Thr Leu Ile Asp Ala Leu Leu Gly Asp Pro His Cys Asp Gly Phe Gln
                85                  90                  95
Asn Lys Lys Trp Asp Leu Phe Val Glu Arg Ser Lys Ala Tyr Ser Asn
                100                 105                 110
Cys Tyr Pro Tyr Asp Val Pro Asp Tyr Ala Ser Leu Arg Ser Leu Val
            115                 120                 125
Ala Ser Ser Gly Thr Leu Glu Phe Ile Asn Glu Ser Phe Asn Trp Thr
        130                 135                 140
Gly Val Thr Gln Asn Gly Gly Ser Ser Ala Cys Lys Arg Gly Ser Asp
145                 150                 155                 160
Asn Ser Phe Phe Ser Arg Leu Asn Trp Leu His Glu Leu Glu Tyr Lys
                165                 170                 175
Tyr Pro Ala Leu Asn Val Thr Met Pro Asn Asn Glu Lys Phe Asp Lys
                180                 185                 190
Leu Tyr Ile Trp Gly Val His Pro Ser Thr Asp Lys Asp Gln Thr
            195                 200                 205
Ser Leu Tyr Val Gln Ala Ser Gly Arg Val Thr Val Ser Thr Lys Arg
        210                 215                 220
Ser Gln Gln Thr Val Ile Pro Asn Ile Gly Ser Arg Pro Trp Val Arg
225                 230                 235                 240
```

```
Gly Leu Ser Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
        260                 265                 270

Tyr Phe Lys Ile Arg Ser Gly Lys Ser Ser Ile Met Arg Ser Asp Ala
    275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 13
<211> LENGTH: 566
<212> TYPE: PRT
<213> ORGANISM: Artificial Sequence
<220> FEATURE:
<223> OTHER INFORMATION: Synthetic Construct

<400> SEQUENCE: 13

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30
```

-continued

```
His His Ala Val Pro Asn Gly Thr Leu Val Lys Thr Ile Thr Asn Asp
         35                  40                  45

Gln Ile Glu Val Thr Asn Ala Thr Glu Leu Val Gln Ser Ser Ser Thr
 50                  55                  60

Gly Arg Ile Cys Asp Ser Pro His Arg Ile Leu Asp Gly Glu Asn Cys
 65                  70                  75                  80

Thr Leu Ile Asp Ala Leu Leu Gly Asp Pro His Cys Asp Gly Phe Gln
                 85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
             115                 120                 125

Ala Ser Ser Gly Thr Leu Glu Phe Ile Asn Glu Ser Phe Asn Trp Thr
130                 135                 140

Gly Val Thr Gln Asn Gly Gly Ser Ser Ala Cys Lys Arg Gly Ser Val
145                 150                 155                 160

Asn Ser Phe Phe Ser Arg Leu Asn Trp Leu Thr Lys Leu Lys Tyr Lys
                165                 170                 175

Tyr Pro Ala Leu Asn Val Thr Met Pro Asn Asn Asp Lys Phe Asp Lys
             180                 185                 190

Leu Tyr Ile Trp Gly Val His His Pro Ser Thr Asp Gln Asp Gln Thr
         195                 200                 205

Ser Leu Tyr Val Gln Ala Ser Gly Arg Val Thr Val Ser Thr Lys Arg
     210                 215                 220

Ser Gln Gln Thr Val Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
             260                 265                 270

Tyr Phe Lys Ile Arg Ser Gly Lys Ser Ser Ile Met Arg Ser Asp Ala
         275                 280                 285

Pro Ile Gly Thr Cys Asn Ser Glu Cys Ile Thr Pro Asn Gly Ser Ile
     290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
             340                 345                 350

Gly Phe Ile Glu Asn Gly Trp Glu Gly Met Val Asp Gly Trp Tyr Gly
         355                 360                 365

Phe Arg His Gln Asn Ser Glu Gly Thr Gly Gln Ala Ala Asp Leu Lys
     370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
             420                 425                 430

Lys Ile Asp Leu Trp Ser Tyr Asn Ala Glu Leu Leu Val Ala Leu Glu
         435                 440                 445
```

```
Asn Gln His Thr Ile Asp Leu Thr Asp Ser Glu Met Asn Lys Leu Phe
    450                 455                 460
Glu Lys Thr Arg Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
                500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
    530                 535                 540
Val Val Leu Leu Gly Phe Ile Met Trp Ala Cys Gln Lys Gly Asn Ile
545                 550                 555                 560
Arg Cys Asn Ile Cys Ile
                565
```

<210> SEQ ID NO 14
<211> LENGTH: 566
<212> TYPE: PRT
<213> ORGANISM: Artificial Sequence
<220> FEATURE:
<223> OTHER INFORMATION: Synthetic Construct

<400> SEQUENCE: 14

```
Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
                20                  25                  30
His His Ala Val Pro Asn Gly Thr Leu Val Lys Thr Ile Thr Asn Asp
            35                  40                  45
Gln Ile Glu Val Thr Asn Ala Thr Glu Leu Val Gln Ser Ser Ser Thr
        50                  55                  60
Gly Arg Ile Cys Asp Ser Pro His Arg Ile Leu Asp Gly Lys Asn Cys
65                  70                  75                  80
Thr Leu Ile Asp Ala Leu Leu Gly Asp Pro His Cys Asp Gly Phe Gln
                85                  90                  95
Asn Lys Lys Trp Asp Leu Phe Val Glu Arg Ser Lys Ala Phe Ser Asn
                100                 105                 110
Cys Tyr Pro Tyr Asp Val Pro Asp Tyr Ala Ser Leu Arg Ser Leu Val
            115                 120                 125
Ala Ser Ser Gly Thr Leu Glu Phe Ile Asn Glu Ser Phe Asn Trp Thr
        130                 135                 140
Gly Val Thr Gln Asn Gly Gly Ser Tyr Ala Cys Lys Arg Gly Ser Val
145                 150                 155                 160
Asn Ser Phe Phe Ser Arg Leu Asn Trp Leu His Lys Ser Glu Ser Lys
                165                 170                 175
Tyr Pro Ala Leu Asn Val Thr Met Pro Asn Asn Asp Lys Phe Asp Lys
            180                 185                 190
Leu Tyr Ile Trp Gly Val His His Pro Ser Thr Asp Gln Glu Gln Thr
        195                 200                 205
Ser Leu Tyr Val Gln Ala Ser Gly Arg Val Thr Val Ser Thr Lys Arg
    210                 215                 220
Ser Gln Gln Thr Val Ile Pro Asn Ile Gly Ser Arg Pro Trp Val Arg
225                 230                 235                 240
```

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 15
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 15
aagcttatga agaccatcat cgccctctcc tatatctttt gcctggtgtt cgcccagaac    60
ctgcccggca acgacaatag cacagccaca ctctgtctcg acaccatgc cgtgcccaac    120 ggcacactgg tgaagacaat tacaaatgac cagatcgagg tgaccaatgc caccgaactg    180

-continued

```
gtgcagagca gctccaccgg aaggatttgc gactcccctc acagaatcct ggacggcaag      240
aattgtaccc tgatcgacgc cctgctggga gatcctcatt gtgacggctt ccagaacgaa      300
aagtgggacc tgttcgtgga gaggtccaag gctttcagca attgctaccc ctacgacgtc      360
cctgattacg ccagcctgag gagcctggtg ccagcagcg gcacactgga attcatcaac       420
gaaggcttca actggaccgg agtgacccag tccggaggct cctacgcctg caagaggga       480 agcgacaaca gcttcttcag cagactcaac tggctgtacg agtccgaaag caagtacccc      540
gccctgaacg tgaccatgcc caataacggc aacttcgaca aactgtacat ctggggcgtc      600
catcacccca gcaccgacaa ggagcaaaca aacctctacg tgagggcttc cggaagggtc      660
accgtgtcca ccaagagaag ccagcagacc gtgatcccca atattggcag caggccctgg      720
gtgagaggcc tgagcagcag gatcagcatc tactggacca tcgtcaagcc cggcgacatc      780
ctgctcatta actccacagg caacctcatc gcccctagag gctacttcaa gatcaggacc      840
ggcaagtcct ccatcatgag gagcgatgcc cctatcggca cctgtagcag cgagtgcatt      900 accccaacg gctccatccc taacgacaag cctttccaga cgtcaacaa gattacatac        960 ggcgcctgtc ccaagtacgt gaagcagaac ccctgaagc tggccaccgg aatgaggaac      1020 gtgccgaga agcagacaag gggcattttc ggcgccatcg ccggcttcat tgaaaacgga      1080
tgggagggca tggtggatgg ctggtatggc tttagacacc agaatagcga gggcacaggc      1140
caggccgccg acctcaaaag cacccaggcc gccatcgacc agatcaatgg caagctgaac      1200
aggctgatcg agaagacaaa tgagaagttt caccagatcg agaaggagtt cagcgaagtg      1260
gagggcagga ttcaggatct cgaaaagtac gtggaggaca ccaaaatcga cctctggtcc      1320
tacaatgccg agctgctggt ggccctcgag aatcagcata ccatcgacct gacagatagc      1380
gagatgaata agctgtttga aaagaccaga aaacagctga gggagaatgc gaagacatg      1440 ggaaatggct gcttcaaaat ctatcacaag tgcgataatg cctgcatcgg cagcatcagg      1500
aacggcacct acgaccacga cgtgtacagg gacgaggccc tcaataatag gttccagatc      1560
aagggcgtgg agctgaagtc cggatacaag gactggatac tgtggatttc cttcgccatc      1620
agctgttttc tgctgtgcgt cgtgctgctg ggattcatca tgtgggcctg ccagaaggga      1680
aatatcagat gtaacatctg catctgatag ggatcc                                 1716
```

<210> SEQ ID NO 16
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 16

```
aagcttatga agaccatcat cgccctgtcc tacatcttct gcctggtgtt cgcccaaaag      60
ctgcctggca acgataactc cacagccacc ctgtgtctgg acaccacgc tgtgcctaac       120 ggaaccctgg tcaagaccat caccaacgac cagatcgagg tgaccaacgc caccgagctg      180
gtccaaagca gctccaccgg cagaatttgc gacagccccc acagaatcct ggacggaaag      240
aattgcaccc tgatcgacgc cctcctggga gatcccattg cgacggctt ccagaacgaa       300 gagtgggacc tgtttgtgga aagaagcaag gcctactcca actgctaccc ttacgacgtc      360
cctgattacg cctcctgag atccctggtg gcctcctccg gcaccctgga gttcattaac      420
gaggatttta attggaccgg cgtggcccag agcggaggca gctatgcctg taagagagga      480
agcgtgaaca gcttcttctc caggctgaac tggctccacg agagcgaata caagtacccc      540
```

```
gccctgaacg tgacaatgcc caacaacggc aagtttgata agctgtacat ctggggcgtc    600
catcacccct ccacagacag ggagcaaacc aatctgtacg tgagggcttc cggaagagtg    660
accgtgtcca ccaagaggtc ccagcagacc gtgatcccca acatcgggag caggccctgg    720
gtgagaggcc tctccagcag aatcagcatc tactggacca tcgtcaagcc cggagacatc    780
ctgctgatca acagcaccgg caacctgatc gcccctagag gctatttcaa gatcaggacc    840
ggcaagagca gcatcatgag gagcgacgct cccatcggca cctgctcctc cgagtgtatc    900
acacccaacg gcagcatccc taacgacaag cctttccaga acgtcaacaa gatcacctac    960
ggcgcctgcc ctagatacgt gaagcagaac accctgaagc tggccaccgg aatgaggaac   1020
gtgcccgaaa agcagaccag gggaattttc ggcgccattg ccggattcat cgagaacgga   1080
tgggagggaa tggtggacgg ctggtacggc tttaggcacc agaactccga gggcacaggc   1140
caagccgccg acctcaaatc cacccaggcc gccatcgacc agatcaacgg caagctgaac   1200
agactgatcg aaaagaccaa cgagaagttc caccagatcg agaaggaatt ctccgaggtg   1260
gagggaagaa tccaggacct cgagaagtac gtggaagaca ccaagatcga cctgtggagc   1320
tacaacgccg aactcctcgt ggctctggag aatcagcaca ccattgacct gaccgacagc   1380
gagatgaaca agctgttcga gaaaaccagg aagcagctga gagagaacgc cgaggatatg   1440
ggaaatggct gtttcaagat ctaccataaa tgcgacaacg cctgcatcgg aagcatcagg   1500
aacggcacct acgaccacga cgtctacagg gacgaagccc tgaataatag gttccagatc   1560
aaaggcgtgg agctcaagag cggctataag gactggatac tgtggatttc cttcgccatc   1620
agctgttttc ctgctgtgcgt ggtcctgctg ggattcatca tgtgggcctg ccagaaggga   1680
aacatcaggt gcaacatctg tatctaatag ggatcc                             1716
```

<210> SEQ ID NO 17
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 17

```
aagcttatga agaccatcat tgccctgtcc tacatcctgt gcctggtctt tgcccagaag     60
ctgcccggca acgacaactc cacagccacc ctgtgtctgg ccaccatgc cgtgcccaac    120 ggaaccctcg tgaagaccat taccaacgac cagatcgagg tgaccaatgc caccgagctg    180
gtccagagca gcagcaccgg cagaatctgc gacagccccc accaaatcct ggatggcgaa    240
aattgcaccc tgatcgatgc cctcctgggc gaccccact gtgatggctt ccagaacaag    300
gagtgggacc tcttcgtgga aaggagcaag gcttactcca actgctaccc ctatgacgtg    360
cccgactacg cctccctgag gtccctcgtc gccagcagcg gaaccctcga attcaacaac    420
gagagcttca actggaccgg agtcgcccag aatggcacca gcagcgcctg taagaggagg    480
tccatcaaga gcttcttcag caggctgaac tggctccacc agctgaagta taaataccccc    540 gccctgaacg tcaccatgcc caacaatgag aagttcgaca agctgtacat ttggggagtg    600 catcaccccta gcaccgatag cgaccaaatc tccctgtatg cccaggccag cggcagagtg    660
acagtgtcca caaagaggag ccagcagacc gtcattccca atattggcag cagaccttgg    720
gtgagaggcg tcagctccag gatctccatt tattggacca tcgtgaagcc tggcgacatc    780
ctcctcatca actccacagg caatctgatc gctcccaggg gctatttaa gattaggtcc    840
```

| | |
|---|---|
| ggcaagagca gcatcatgag gagcgacgcc cctatcggca agtgcaacag cgagtgtatc | 900 |
| accccaacg gcagcattcc caacgacaaa cccttccaga acgtgaacag gatcacctac | 960 |
| ggcgcctgcc ctagatacgt gaagcagaac accctgaagc tggccaccgg aatgaggaac | 1020 |
| gtgcccgaaa agcagaccag gggaattttc ggcgccattg ccggattcat cgagaacgga | 1080 |
| tgggagggaa tggtggacgg ctggtacggc tttaggcacc agaactccga gggcacaggc | 1140 |
| caagccgccg acctcaaatc cacccaggcc gccatcaatc agattaacgg caaactgaat | 1200 |
| aggctgattg aaaaaacaaa cgagaaattc catcagattg agaaagagtt cagcgaggtg | 1260 |
| gaaggcagaa tacaggacct ggagaagtac gtggaagaca ccaagatcga cctctggtcc | 1320 |
| tacaatgctg agctgctggt cgccctggag aatcagcaca ccatcgacct caccgacagc | 1380 |
| gagatgaata gctccttcga gaggaccaag aagcagctga gagagaacgc cgaggacatg | 1440 |
| ggcaatggct gcttcaagat ctatcacaag tgcgacaacg cctgtatcgg cagcatcaga | 1500 |
| aacggcacat acgatcacga cgtgtacagg gacgaggctc tcaacaacag gttccaaatt | 1560 |
| aagggcgtcg agctcaagag cggctacaag gactggatac tgtggattag cttcgccatc | 1620 |
| agctgctttc tgctgtgtgt ggtgctcctc ggcttcatca tgtgggcctg ccagaagggc | 1680 |
| aatatcaggt gcaacatttg catttaatag ggatcc | 1716 |

<210> SEQ ID NO 18
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| aagcttatga agaccatcat tgccctgtcc tacatcctgt gcctggtctt tgcccagaag | 60 |
| ctgcccggca acgacaactc cacagccacc ctgtgtctgg gccaccatgc cgtgcccaac | 120 |
| ggaaccctcg tgaagaccat taccaacgac cagatcgagg tgaccaatgc caccgagctg | 180 |
| gtccagagca gcagcaccgg cagaatctgc gacagccccc accaaatcct ggatggcgaa | 240 |
| aattgcaccc tgatcgatgc cctcctgggc gacccccact gtgatggctt ccagaacaag | 300 |
| gagtgggacc tcttcgtgga aaggagcaag gcttactcca actgctaccc ctatgacgtg | 360 |
| cccgactacg cctccctgag gtccctcgtc gccagcagcg gaaccctcga attcaacaac | 420 |
| gagagcttca ctggaccgg agtcgcccag aatggcacca gcagcgcctg taagaggagg | 480 |
| tccatcaaga gcttcttcag caggctgaac tggctccacc agctgaagta taaataccc | 540 |
| gccctgaacg tcaccatgcc caacaatgag aagttcgaca agctgtacat ttggggagtg | 600 |
| catcacccta gcaccgatag cgaccaaatc tccctgtatg cccaggccag cggcagagtg | 660 |
| acagtgtcca caaagaggag ccagcagacc gtcattccca atattggcag cagaccttgg | 720 |
| gtgagaggcg tctccagcag gatttccatc tattggacca tcgtgaaacc cggagacatc | 780 |
| ctgctgatca acagcaccgg caacctgatt gcccccaggg gctatttcaa gatcaggagc | 840 |
| ggcaagtcct ccatcatgag gtccgacgcc cccatcggca gtgtaactc gaatgcatc | 900 |
| accccaacg gctccatccc taacgacaag cccttccaga acgtcaacag gatcaccctat | 960 |
| ggcgcctgcc ccaggtacgt gaaacagaac accctgaaac tcgccacagg catgaggaat | 1020 |
| gtgcccgaga acagacaag gggcatcttc ggcgccatcg ccggatttat tgagaatggc | 1080 |
| tgggaaggca tggtggatgg ctggtacggc ttcaggcatc agaattccga gggcaccgga | 1140 |
| caagccgccg acctcaagtc cacccaggcc gccatcaatc agattaacgg caaactgaat | 1200 |

```
aggctgattg aaaaaacaaa cgagaaattc catcagattg agaaagagtt cagcgaggtg    1260
gaaggcagaa tacaggacct ggagaagtac gtggaagaca ccaagatcga cctctggtcc    1320
tacaatgctg agctgctggt cgccctggag aatcagcaca ccatcgacct caccgacagc    1380
gagatgaata agctcttcga ggaccaag aagcagctga gagagaacgc cgaggacatg      1440
ggcaatggct gcttcaagat ctatcacaag tgcgacaacg cctgtatcgg cagcatcaga    1500
aacggcacat acgatcacga cgtgtacagg gacgaggctc tcaacaacag gttccaaatt    1560
aagggcgtcg agctcaagag cggctacaag gactggatac tgtggattag cttcgccatc    1620
agctgctttc tgctgtgtgt ggtgctcctc ggcttcatca tgtgggcctg ccagaagggc    1680
aatatcaggt gcaacatttg catttgatag ggatcc                              1716
```

<210> SEQ ID NO 19
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 19

```
aagcttatga agaccattat cgccctgtcc tatatcctgt gcctggtgtt tgcccagaaa     60
ctgcccggca acgacaactc caccgccaca ctctgtctgg acaccacgc cgtgcccaac    120 ggcaccatcg tcaaaaccat caccaacgac cagattgagg tcacaaatgc caccgaactg    180
gtgcagagca gcagcaccgg cgagatttgc gactcccctc atcagatcct ggacggcgaa    240
aactgtaccc tgatcgacgc tctcctcggc gaccctcagt gtgacggatt ccagaacaaa    300
aagtgggacc tcttcgtgga gaggtccaag gcttacagca actgctaccc ttacgacgtc    360
cctgactacg cctccctgag gagcctggtc gctagctccg gcaccctgga gttcaacaac    420
gagagcttca ctggacaggg cgtgacccag aacggcacaa gcagcgcctg caagagaagg    480
agcaacaatt ccttctttc caggctcaat tggctgaccc acctgaagtt caagtaccct    540 gcccctcaacg tcaccatgcc caataatgag aagtttgata gctgtatat ctggggagtg    600 caccaccccg gcacagataa cgaccagatc tttctgtacg ctcaggcctc cggaagaatc    660
accgtgagca ccaagagaag ccagcaaacc gtgatcccca acattggctc cagacctagg    720
gtcaggaaca tccctagcag gatcagcatc tattggacca tcgtgaagcc tggcgacatc    780
ctcctgatca actccacagg caacctgatc gcccctaggg gctacttcaa aatcaggagc    840
ggcaaaagca gcatcatgag gagcgatgcc cccatcggaa agtgtaacag cgagtgcatc    900 accccccaacg gctccatccc caacgataaa cccttccaga acgtcaacag gattacctac    960
ggcgcctgtc ccagatacgt gaagcagaac accctgaaac tcgccaccgg catgaggaat   1020
gtccctgaga gcagaccag aggaatcttc ggagccattg ccggctttat cgagaacggc   1080
tgggagggca tggtggatgg ctggtacgga ttcaggcatc agaacagcga gggaattgga   1140
caggccgctg acctcaagtc cacacaggct gccatcaacc agatcaatgg caagctcaac   1200
aggctgatcg gcaagaccaa tgaaaagttt caccagattg agaaggaatt cagcgaggtc   1260
gaaggcagaa tacaggacct ggagaagtac gtggaggaca ccaagatcga cctctggtcc   1320
tataatgccg agctgctggt cgccctggag aatcagcaca caatcgacct gaccgacagc   1380
gagatgaaca aactgttcga aaggaccaaa aagcagctca gggagaacgc cgaggacatg   1440
ggcaatggct gcttcaagat ttatcacaag tgtgacaatg cctgtatcgg gagcatcagg   1500
```

| | |
|---|---|
| aacggcacct acgaccacga cgtgtatagg gacgaggccc tgaacaacag gttccagatc | 1560 |
| aaaggcgtcg agctgaagtc cggatacaag gactggatac tgtggatcag ctttgccatc | 1620 |
| tcctgctttc tgctctgcgt ggccctgctc ggcttcatca tgtgggcctg tcagaagggc | 1680 |
| aatatcagat gcaacatctg catctgatag ggatcc | 1716 |

<210> SEQ ID NO 20
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 20

| | |
|---|---|
| aagcttatga aaaccatcat cgccctgagc tatatcctct gtctggtgtt cgcccagaag | 60 |
| ctgcccggca atgacaactc caccgccaca ctctgtctcg gccatcacgc cgtgcccaac | 120 |
| ggcacaatcg tgaagaccat taccaatgat cagatcgagg tgaccaatgc caccgaactg | 180 |
| gtgcaaagca gcagcaccgg cgagatctgc gacagccctc accagattct ggatggcgag | 240 |
| aactgcacac tcatcgatgc cctgctgggc gaccctcagt gtgacggctt ccagaacaag | 300 |
| aagtgggatc tgttcgtgga gagatccaag gcctacagca actgctaccc ttacgacgtg | 360 |
| cctgactacg cctccctgag gtccctggtc gcctcctccg gaacactgga gttcaacaac | 420 |
| gagagcttta ctggaccggc gtgacacag aacggcacaa gcagcgcctg caagaggagg | 480 |
| agcaacaact ccttcttcag caggctgaac tggctgaccc acctgaaatt caagtacccc | 540 |
| gctctgaacg tcacaatgcc caataacgag aagtttgaca gctgtacat ttggggagtg | 600 |
| catcaccccg gaaccgacaa ggaccagatc ttcctgtatg cccaggcctc cggcaggatt | 660 |
| accgtctcca ccaagaggag ccagcagaca gtgatcccca catcggcag cagacctagg | 720 |
| gtcaggaaca tccccagcag gatctccatc tactggacaa ttgtcaagcc cggcgacatc | 780 |
| ctcctcatca acagcaccgg caacctcatt gcccctagag ctacttcaa gatcagatcc | 840 |
| ggcaagagca gcatcatgag atccgacgcc cccatcggca gtgtaactc cgagtgcatt | 900 |
| accccccaatg gctccattcc caacgacaaa cccttccaga atgtgaacag gatcacatat | 960 |
| ggcgcctgcc ccagatacgt gaagcagaac accctcaagc tggctaccgg catgaggaac | 1020 |
| gtgcccgaaa agcagacaag gggcatcttc ggcgctatcg ctggcttcat cgaaaacgga | 1080 |
| tgggaaggca tggtcgatgg ctggtacggc ttcaggcatc agaactccga aggcaggga | 1140 |
| caagctgccg acctgaagag cacacaggct gccatcaatc agattaacgg caaactgaac | 1200 |
| aggctgatcg gcaaaacaaa tgaaaagttc caccagatcg agaaggaatt cagcgaagtc | 1260 |
| gaaggcagaa tacaggacct ggagaaatac gtggaggaca caaagatcga cctgtggtcc | 1320 |
| tataacgctg agctcctggt ggctctggag aaccaacaca caatcgacct gaccgatagc | 1380 |
| gagatgaaca gctgttcga gaggaccaag aagcagctga gagagaatgc cgaggacatg | 1440 |
| ggcaatggct gctttaaaat ttaccacaaa tgcgacaacg cctgcattgg ctccatcagg | 1500 |
| aacggcacct atgaccacga cgtgtacagg gacgaggccc tcaacaacag gttccagatc | 1560 |
| aagggagtcg agctgaagag cggctacaag gactggatac tgtggatcag ctttgccatc | 1620 |
| tcctgtttcc tcctgtgcgt cgctctgctg ggcttcatta tgtgggcctg ccagaaaggc | 1680 |
| aacattaggt gtaacatctg tatttaatag ggatcc | 1716 |

<210> SEQ ID NO 21
<211> LENGTH: 1716

<212> TYPE: DNA
<213> ORGANISM: Artificial Sequence
<220> FEATURE:
<223> OTHER INFORMATION: Synthetic Construct

<400> SEQUENCE: 21

```
aagcttatga agaccatcat cgctctcagc tacattctgt gcctcgtgtt tgctcagaag      60
ctgcccggca acgataacag caccgccacc ctgtgcctcg ccatcatgc cgtccccaat      120
ggcaccatcg tcaagacaat caccaacgac cagatcgagg tcaccaacgc caccgaactg     180
gtgcaaagct ccagcaccgg cagaatctgc gactccccc accagatcct ggatggagag      240
aactgcaccc tgatcgatgc tctgctggga gaccccact cgacggctt ccagaataag       300
aagtgggacc tgttcgtgga agatccaag gcctactcca actgctaccc ttacgacgtg      360
cccgactacg cctccctgag gtccctggtc gcttcctccg gcaccctgga gttcatcaat     420
gagtccttca ctggaccgg cgtcacccaa aacggcggca gcagcgcttg taaaaggggc      480
agcaataact ccttcttcag caggctgaac tggctgaccc atctggagta caagtacccc    540
gccctgaatg tgaccatgcc caacaacgag aagttcgata agctctatat ctggggcgtg    600
caccaccccg gaacagacaa ggatcagatc agcctgtacg ctcaggcctc cggaaggatt    660
acagtctcca ccaagaggag ccagcagaca gtcatcccca acatcggcag caggcccagg    720
gtgagaggcc tgagctccag gatctccatt tattggacca tcgtgaagcc tggcgacatc    780
ctcctcatca actccacagg caatctgatc gctcccaggg gctattttaa gattaggtcc    840
ggcaagagca gcatcatgag gagcgacgcc cctatcggca gtgcaacag cgagtgtatc    900
accccccaacg gcagcattcc caacgacaaa cccttccaga acgtgaacag gatcacctac    960
ggcgcctgcc ctagatacgt gaagcagaac accctgaagc tggccaccgg aatgaggaac   1020
gtgcccgaaa gcagaccag gggaattttc ggcgccattg ccggattcat cgagaacgga    1080
tgggagggaa tggtggacgg ctggtacggc tttaggcacc agaactccga gggcacaggc    1140
caagccgccg acctcaaatc cacccaggcc gccatcgacc agatcaacgg caagctgaac    1200
agactgatcg aaaagaccaa cgagaagttc caccagatcg agaaggaatt ctccgaggtg   1260
gagggaagaa tccaggacct cgagaagtac gtggaagaca ccaagatcga cctgtgggca    1320
tacaacgccg aactcctcgt ggctctggag aatcagcaca ccattgacct gaccgacagc    1380
gagatgaaca agctgttcga gaaaaccaag aaacagctga gagaaaacgc cgaggacatg    1440
ggcaatggat gcttcaagat ttaccataag tgcgacaacg cttgtatcgg gagcatcagg    1500
aatggcacct acgatcatga cgtgtacagg gacgaggccc tgaacaacag gttccagatc    1560
aaaggcgtgg agctcaaatc cggctataag gattggatac tgtggatctc cttcgctatc   1620
tcctgcttcc tgctgtgcgt cgccctgctg ggcttcatca tgtgggcctg ccagaaggga    1680
aacatcagat gtaacatctg tatttaatag ggatcc                             1716
```

<210> SEQ ID NO 22
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 22

```
aagcttatga aaacaatcat cgccctctcc tatatcctgt gcctggtgtt cgctcaaaag      60
ctccccggca acgacaacag caccgctaca ctgtgtctgg gccaccacgc cgtccccaac    120
```

```
ggaaccatcg tgaagaccat caccaacgac caaatcgagg tgaccaacgc caccgagctc   180
gtgcagtcca gcagcaccgg cgagatttgc gatagccctc atcagatcct ggacggcgag   240
aactgcaccc tgatcgacgc tctgctgggc gacccccagt gtgacggatt tcagaacaag   300
aaatgggacc tcttcgtgga gaggtccaag gcctactcca actgctaccc ctacgacgtc   360
cccgattacg cctccctgag gagcctggtg gctagctccg gcaccctcga attcaacaac   420
gagtccttca actggacagg cgtcacccag aatggaacct cctccgcctg catcaggaga   480
tccaataaca gcttcttcag caggctgaat tggctcacac acctgaactt caagtacccc   540
gccctcaacg tgaccatgcc caacaacgag cagttcgaca gctctacat ctggggcgtc   600
catcaccctg gcaccgacaa ggatcaaatc ttcctctacg cccaggcctc cggcagaatc   660
accgtcagca ccaagaggtc ccagcagaca gtcatcccca catcggctc caggcccagg   720
gtgaggaaca tccccagcag aatctccatc tactggacca tcgtgaaacc cggagacatt   780
ctcctgatta acagcaccgg caacctgatc gcccctaggg gctactttaa gatcaggtcc   840
ggaaaaagca gcatcatgag gtccgacgct cccatcggca agtgcaactc cgagtgcatt   900
acacccaatg gcagcatccc taacgacaag cctttccaga atgtgaacag gatcacatac   960
ggcgcctgcc ctaggtatgt gaaacagaac accctgaagc tggccaccgg catgaggaat  1020
gtgcctgaga agcagaccag gggcatttc ggcgccattg ctggcttcat cgagaacggc  1080
tgggagggaa tggtgacgg ctggtacggc ttcagacacc agaatagcga aggcaggga  1140
caggccgccg acctgaaaag cacccaggcc gccatcgatc agattaacgg aaagctgaac  1200
agactgatcg gaaagacaaa cgaaaagttt caccagatcg agaaggagtt cagcgaggtg  1260
gaaggcagga ttcaagacct ggagaagtac gtcgaagaca ccaagatcga cctgtggagc  1320
tacaatgccg agctgctcgt ggctctcgag aaccagcaca ccatcgacct gaccgactcc  1380
gagatgaaca agctgttcga gaagaccaag aagcagctga gggagaacgc cgaagatatg  1440
ggaaacggct gctttaagat ctatcacaag tgtgacaacg cctgcatcgg cagcatcagg  1500
aacggcacat acgatcacga tgtgtacaga gacgaggctc tcaacaacag gttccagatc  1560
aagggcgtgg agctcaagtc cggatacaag gactggatac tgtggattag cttcgccatc  1620
tcctgctttc tcctgtgtgt ggccctgctg ggctttatca tgtgggcctg ccagaagggc  1680
aatatcagat gcaacatctg catctgatag ggatcc                            1716
```

<210> SEQ ID NO 23
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 23

```
aagcttatga aaacaatcat cgccctctcc tatatcctgt gcctggtgtt cgctcaaaag    60
ctccccggca acgacaacag caccgctaca ctgtgtctgg ccaccacgc cgtccccaac   120
ggaaccatcg tgaagaccat caccaacgac caaatcgagg tgaccaacgc caccgagctc   180
gtgcagtcca gcagcaccgg cgagatttgc gatagccctc atcagatcct ggacggcgag   240
aactgcaccc tgatcgacgc tctgctgggc gacccccagt gtgacggatt tcagaacaag   300
aaatgggacc tcttcgtgga gaggtccaag gcctactcca actgctaccc ctacgacgtc   360
cccgattacg cctccctgag gagcctggtg gctagctccg gcaccctcga attcaacaac   420
gagtccttca actggacagg cgtcacccag aatggaacct cctccgcctg catcagggc    480
```

```
tccaataaca gcttcttcag caggctgaat tggctcacac acctgaactt caagtacccc       540
gccctcaacg tgaccatgcc caacaacgag cagttcgaca agctctacat ctggggcgtc       600
catcaccctg caccgacaa ggatcaaatc ttcctctacg cccaggcctc cggcagaatc        660
accgtcagca ccaagaggtc ccagcaggcc gtcatcccca catcggctc caggcccagg        720 atcaggaaca tccccagcag aatctccatc tactggacca tcgtgaaacc cggagacatt      780
ctcctgatta acagcaccgg caacctgatc gcccctaggg gctactttaa gatcaggtcc      840 ggaaaagca gcatcatgag gtccgacgct cccatcggca agtgcaactc cgagtgcatt       900
acacccaatg gcagcatccc taacgacaag ccttttccaga atgtgaacag gatcacatac    960
ggcgcctgcc ctaggtatgt gaaacagagc accctgaagc tggccaccgg catgaggaat     1020
gtgcctgaga agcagaccag gggcattttc ggcgccattg ctggcttcat cgagaacggc     1080
tgggagggaa tggtggacgg ctggtacggc ttcagacacc agaatagcga aggcagggga     1140
caggccgccg acctgaaaag cacccaggcc gccatcgatc agattaacgg aaagctgaac     1200
agactgatcg gaaagacaaa cgaaaagttt caccagatcg agaaggagtt cagcgaggtg     1260
gaaggcagga ttcaagacct ggagaagtac gtcgaagaca ccaagatcga cctgtggagc     1320
tacaatgccg agctgctcgt ggctctcgag aaccagcaca ccatcgacct gaccgactcc     1380
gagatgaaca gctgttcga gaagaccaag aagcagctga gggagaacgc cgaagatatg      1440
ggaaacggct gctttaagat ctatcacaag tgtgacaacg cctgcatcgg cagcatcagg     1500
aacggcacat acgatcacga tgtgtacaga gacgaggctc tcaacaacag gttccagatc     1560
aagggcgtgg agctcaagtc cggatacaag gactggatac tgtggattag cttcgccatc     1620
tcctgctttc tcctgtgtgt ggccctgctg ggctttatca tgtgggcctg ccagaagggc     1680
aatatcagat gcaacatctg catctgatag ggatcc                              1716
```

<210> SEQ ID NO 24
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 24

```
aagcttatga agaccatcat tgccctctcc tacatcctgt gtctcgtgtt cgcccagaag       60
ctgcccggca cgacaattc caccgccaca ctctgcctgg acaccacgc cgtgcccaat        120 ggcaccctgg tgaagacaat cacaaacgat cagatcgagg tgaccaatgc cacagagctg     180
gtgcagtcca gcagcacagg aaggatctgc gacagccctc acagaatcct ggacggcgaa     240
aactgcaccc tgatcgacgc cctgctgggc gatcctcact gtgacggctt ccagaacaag      300
aagtgggacc tcttcgtgga gagatccaag gcctactcca actgttaccc ttacgacgtg     360
cccgactatg ctagcctgag atccctggtg gctagcagcg gcacactgga gttcattaac     420
gagagcttca actggaccgg cgtgacccaa atggcggca gctccgcctg caagagaggc      480
agcgacaata gcttcttcag cagactgaac tggctgcacg agctggagta caagtacccc    540
gctctgaacg tgaccatgcc taataatgag aaattcgata aactgtacat ttggggcgtg    600
caccacccct ccaccgacaa ggatcagacc agcctgtatg tgcaggcctc cggcagagtg    660
acagtgtcca ccaagaggag ccaacagacc gtgattccca atatcggcag cagaccctgg    720 gtcagggag tcagcagcag gatcagcatc tactggacaa ttgtcaagcc cggcgatatc    780
```

-continued

| | |
|---|---|
| ctgctgatca acagcacagg caacctgatc gcccctaggg gctatttcaa gatcaggtcc | 840 |
| ggcaagagca gcatcatgag atccgacgct cccatcggca agtgcaactc cgaatgcatt | 900 |
| accccaacg gcagcatccc caatgacaag cccttccaga acgtcaacag aatcacctac | 960 |
| ggcgcttgcc ctaggtacgt gaaacagaac accctcaaac tcgccaccgg catgaggaac | 1020 |
| gtgcctgaga agcagaccag gggcattttt ggcgctatcg ctggcttcat cgagaatgga | 1080 |
| tgggagggca tggtggacgg ctggtatggc ttcaggcacc agaatagcga gggaacagga | 1140 |
| caggccgccg acctgaaatc cacacaggcc gccatcgacc agatcaatgg caaactcaat | 1200 |
| aggctcatcg aaaagaccaa cgagaagttt catcagatcg agaaggagtt ctccgaggtg | 1260 |
| gaaggaagaa tccaggacct ggagaagtac gtggaggaca ccaagatcga cctgtggagc | 1320 |
| tacaacgccg agctgctggt ggctctggag aaccagcaca ccattgatct gaccgatagc | 1380 |
| gagatgaaca agctgttcga gaaaaccaga agcagctca gggagaacgc cgaggacatg | 1440 |
| ggcaacggat gtttcaagat ctaccacaag tgcgacaacg cctgtatcgg cagcattagg | 1500 |
| aacggcacct acgaccacga tgtgtatagg acgaggccc tgaacaacag atttcaaatc | 1560 |
| aagggcgtcg aactcaagtc cggctacaag gactggatac tgtggatctc cttcgccatc | 1620 |
| tcctgcttcc tcctgtgcgt ggtgctgctc ggcttcatca tgtgggcttg ccagaagggc | 1680 |
| aacatcaggt gcaacatctg tatctgatag ggatcc | 1716 |

<210> SEQ ID NO 25
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 25

| | |
|---|---|
| aagcttatga aaaccatcat cgctctgtcc tacatcttct gtctcgtgtt cgcccagaag | 60 |
| ctgcccggaa acgataacag caccgctacc ctgtgcctgg acaccatgc tgtgcccaac | 120 |
| ggaacccctcg tgaagacaat caccaatgac cagatcgaag tcaccaacgc caccgagctg | 180 |
| gtccagtcca gctccaccgg cagaatttgc gactccccc acagaattct ggacggcaaa | 240 |
| aactgcaccc tgatcgacgc tctcctgggc gacccccatt gcgacggctt ccaaaacgaa | 300 |
| gagtgggacc tgttcgtgga gaggtccaaa gccttcagca actgctatcc ctacgacgtg | 360 |
| cctgattacg cctcccctcag aagcctggtc gcctcctccg gcacactgga gttcatcaac | 420 |
| gaaggcttca ctggaccggg cgtggctcag aatggcggca gctccgcttg caaaagggc | 480 |
| tccgtcaaca gcttcttcag caggctgaac tggctccata aactggaatc caagtaccct | 540 |
| gccctgaacg tgaccatgcc caacaatggc aagttcgaca agctgtacat ctggggagtg | 600 |
| caccaccca gcaccgacaa ggaccagaca atctgtacg tgcaggcttc cggaagagtg | 660 |
| accgtgtcca ccaagaggtc ccagcagacc gtgatcccca acatcgggag caggccctgg | 720 |
| gtgagaggcc tctccagcag aatcagcatc tactggacca tcgtcaagcc cggagacatc | 780 |
| ctgctgatca acagcaccgg caacctgatc gcccctagag gctatttcaa gatcaggacc | 840 |
| ggcaagagca gcatcatgag gagcgacgct cccatcggca cctgctcctc cgagtgtatc | 900 |
| acacccaacg gcagcatccc taacgacaag cctttccaga acgtcaacaa gatcacctac | 960 |
| ggcgcctgcc ctagatacgt gaagcagaac accctgaagc tggccaccgg aatgaggaac | 1020 |
| gtgcccgaaa agcagaccag gggaattttc ggcgccattg ccggattcat cgagaacgga | 1080 |
| tgggagggaa tggtggacgg ctggtacggc tttaggcacc agaactccga gggcacaggc | 1140 |

| | |
|---|---|
| caagccgccg acctcaaatc cacccaggcc gccatcgacc agatcaacgg caagctgaac | 1200 |
| agactgatcg aaaagaccaa cgagaagttc caccagatcg agaaggaatt ctccgaggtg | 1260 |
| gagggaagaa tccaggacct cgagaagtac gtggaagaca ccaagatcga cctgtggagc | 1320 |
| tacaacgccg aactcctcgt ggctctggag aatcagcaca ccattgacct gaccgacagc | 1380 |
| gagatgaaca agctgttcga gaaaaccagg aagcagctga gagagaacgc cgaggatatg | 1440 |
| ggaaatggct gtttcaagat ctaccataaa tgcgacaacg cctgcatcgg aagcatcagg | 1500 |
| aacggcacct acgaccacga cgtctacagg gacgaagccc tgaataatag gttccagatc | 1560 |
| aaaggcgtgg agctcaagag cggctataag gactggatac tgtggatttc cttcgccatc | 1620 |
| agctgtttcc tgctgtgcgt ggtcctgctg ggattcatca tgtgggcctg ccagaaggga | 1680 |
| aacatcaggt gcaacatctg tatctaatag ggatcc | 1716 |

<210> SEQ ID NO 26
<211> LENGTH: 1716
<212> TYPE: DNA
<213> ORGANISM: Artificial Sequence
<220> FEATURE:
<223> OTHER INFORMATION: Synthetic Construct

<400> SEQUENCE: 26

| | |
|---|---|
| aagcttatga aaaccatcat tgccctctcc tacatctttt gcctggtgtt tgcccagaag | 60 |
| ctccctggca acgacaacag caccgccaca ctgtgcctgg acaccatgc tgtgcccaat | 120 |
| ggaaccctcg tgaagaccat caccaatgac cagatcgagg tgaccaatgc cacagaactg | 180 |
| gtgcagagct ccagcaccgg caggatctgt gatagccccc acagaatcct ggacggcaaa | 240 |
| aactgcacac tgatcgacgc tctcctggga gaccccact gtgacggctt tcagaacaag | 300 |
| gagtgggatc tgtttgtcga gagatccaag gcttactcca attgctaccc ttacgacgtg | 360 |
| cccgactatg ccagcctcag gagcctggtg gccagtccg aaccctgga gttcatcaac | 420 |
| gagggcttta attggaccgg cgtgacccaa aatggcggct cctccgcctg taagaggggc | 480 |
| tccgtgaact ccttcttcag caggctgaat tggctgcaca agctggagtc caagtatccc | 540 |
| gccctgaacg tcaccatgcc caacaacgac aagtttgata aactctacat ctggggagtg | 600 |
| caccacccca gcacagacaa ggaccagaca agcctgtacg tccaggcttc cggaagggtg | 660 |
| accgtgtcca ccaagaggag ccagcagacc gtgatcccta atatcggcag caggccctgg | 720 |
| gtcagaggcc tgtccagcag gatcagcatc tactggacca ttgtgaagcc cggagacatc | 780 |
| ctcctgatta actccaccgg caacctgatc gctcccaggg gctactttaa aattaggacc | 840 |
| ggaaagagca gcatcatgag gtccgacgcc ctatcggca catgcaactc cgagtgcatt | 900 |
| accccccaacg gaagcattcc caatgacaag ccttttcaga acgtcaacag gatcaccctac | 960 |
| ggcgcctgcc ctagatacgt gaagcagaac accctgaagc tggccaccgg aatgaggaac | 1020 |
| gtgcccgaaa agcagaccag ggaattttc ggcgccattg ccggattcat cgagaacgga | 1080 |
| tgggagggaa tggtggacgg ctggtacggc tttaggcacc agaactccga gggcacaggc | 1140 |
| caagccgccg acctcaaatc cacccaggcc gccatcgacc agatcaacgg caagctgaac | 1200 |
| agactgatcg aaaagaccaa cgagaagttc caccagatcg agaaggaatt ctccgaggtg | 1260 |
| gagggaagaa tccaggacct cgagaagtac gtggaagaca ccaagatcga cctgtggagc | 1320 |
| tacaacgccg aactcctcgt ggctctggag aatcagcaca ccattgacct gaccgacagc | 1380 |
| gagatgaaca agctgttcga gaaaaccagg aagcagctga gagagaacgc cgaggatatg | 1440 |

-continued

```
ggaaatggct gtttcaagat ctaccataaa tgcgacaacg cctgcatcgg aagcatcagg    1500
aacggcacct acgaccacga cgtctacagg gacgaagccc tgaataatag gttccagatc    1560
aaaggcgtgg agctcaagag cggctataag gactggatac tgtggatttc cttcgccatc    1620
agctgtttcc tgctgtgcgt ggtcctgctg ggattcatca tgtgggcctg ccagaaggga    1680
aacatcaggt gcaacatctg tatctaatag ggatcc                              1716
```

<210> SEQ ID NO 27
<211> LENGTH: 449
<212> TYPE: PRT
<213> ORGANISM: Artificial Sequence
<220> FEATURE:
<223> OTHER INFORMATION: Synthetic Construct

<400> SEQUENCE: 27

```
Met Asn Pro Asn Lys Lys Ile Ile Thr Ile Gly Ser Ile Cys Met Val
1               5                   10                  15

Thr Gly Met Val Ser Leu Met Leu Gln Ile Gly Asn Leu Ile Ser Ile
                20                  25                  30

Trp Val Ser His Ser Ile His Thr Gly Asn Gln His Lys Ala Glu Pro
            35                  40                  45

Ile Ser Asn Thr Asn Phe Leu Thr Glu Lys Ala Val Ala Ser Val Lys
        50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320
```

```
Asn Gly Ala Tyr Gly Val Lys Gly Phe Ser Phe Lys Tyr Gly Asn Gly
            325                 330                 335

Val Trp Ile Gly Arg Thr Lys Ser Thr Asn Ser Arg Ser Gly Phe Glu
        340                 345                 350

Met Ile Trp Asp Pro Asn Gly Trp Thr Glu Thr Asp Ser Ser Phe Ser
            355                 360                 365

Val Lys Gln Asp Ile Val Ala Ile Thr Asp Trp Ser Gly Tyr Ser Gly
        370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
            405                 410                 415

Trp Thr Ser Gly Ser Ser Ile Ser Phe Cys Gly Val Asn Ser Asp Thr
            420                 425                 430

Val Gly Trp Ser Trp Pro Asp Gly Ala Glu Leu Pro Phe Thr Ile Asp
        435                 440                 445

Lys

<210> SEQ ID NO 28
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 28
atgaatccta taagaagat catcacaatc ggaagcatct gcatggtgac aggaatggtg      60
agcctgatgc tgcagatcgg aaatctgatc agcatctggg tgagccacag catccacaca     120
ggaaatcagc acaaggccga gcctatcagc aatacaaatt ttctgacaga aaggccgtg     180 gccagcgtga agctggccgg aaatagcagc ctgtgcccta tcaatggatg ggccgtgtac    240
agcaaggata tagcatcag aatcggaagc aagggagatg tgtttgtgat cagagagcct     300
tttatcagct gcagccacct ggagtgcaga acatttttc tgacacaggg agccctgctg     360
aatgataagc acagcaatgg aacagtgaag atagaagcc ctcacagaac actgatgagc     420
tgccctgtgg gagaggcccc tagcccttac aatagcagat ttgagagcgt ggcctggagc     480
gccagcgcct gccacgatgg aacaagctgg ctgacaatcg gaatcagcgg acctgataat    540
ggagccgtgg ccgtgctgaa gtacaatgga atcatcacag atacaatcaa gagctggaga    600
aataatatcc tgagaacaca ggagagcgag tgcgcctgcg tgaatggaag ctgctttaca    660
gtgatgacag atggacctag caatggacag gccagccaca agatctttaa gatggagaag    720
ggaaaggtgg tgaagagcgt ggagctggat gcccctaatt accactacga ggagtgcagc    780
tgctaccctg atgccggaga gatcacatgc gtgtgcagag ataattggca cggaagcaat    840
agaccttggg tgagctttaa tcagaatctg gagtaccaga tcggatacat ctgcagcgga    900
gtgtttggag ataatcctag acctaatgat ggaacaggaa gctgcggacc tgtgagcagc    960
aatggagcct acggagtgaa gggatttagc tttaagtacg gaaatggagt gtggatcgga   1020
agaacaaaga gcacaaatag cagaagcgga tttgagatga tctgggaccc taatggatgg   1080
acagagacag atagcagctt tagcgtgaag caggatatcg tggccatcac agattggagc   1140
ggatacagcg gaagctttgt gcagcaccct gagctgacag actgggattg catcagacct   1200
tgcttttggg tggagctgat cagaggaaga cctaaggaga gcacaatctg gacaagcgga   1260
```

```
agcagcatca gcttttgcgg agtgaatagc gatacagtgg gatggagctg gcctgatgga    1320
gccgagctgc cttttacaat cgataagtga                                    1350
```

<210> SEQ ID NO 29
<211> LENGTH: 252
<212> TYPE: PRT
<213> ORGANISM: Artificial Sequence
<220> FEATURE:
<223> OTHER INFORMATION: Synthetic Construct

<400> SEQUENCE: 29

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 30
<211> LENGTH: 759
<212> TYPE: DNA
<213> ORGANISM: Artificial Sequence
<220> FEATURE:
<223> OTHER INFORMATION: Synthetic Construct

<400> SEQUENCE: 30

```
atgagcctgc tgaccgaggt ggagacatac gtgctgtcca tcatccccag cggccctctg    60
aaggccgaga tcgcccagag actggaagat gtgttcgccg gcaagaacac cgacctggaa   120
gtgctgatga atggctgaa aaccagaccc atcctgagcc ctctgaccaa ggcatcctg     180 ggcttcgtgt tcaccctgac cgtgcccagc gagagaggcc tgcagaggcg gagattcgtg   240
```

-continued

```
cagaacgccc tgaacggcaa cggcgacccc aacaacatgg acaaggccgt gaagctgtac      300
agaaagctga agcgggagat caccttccac ggcgccaaag agatcagcct gagctacagc      360
gctggcgccc tggccagctg catgggcctg atctacaaca gaatgggcgc cgtgaccacc      420
gaggtggcct tcggcctggt ctgcgccacc tgcgagcaga tcgccgacag ccagcacaga      480
tcccacagac agatggtcac caccaccaac ccCctgatca gacacgagaa cagaatggtg      540
ctggcctcta ccaccgccaa ggccatggaa cagatggccg gcagcagcga gcaggccgcc      600
gaggctatgg aagtcgcctc tcaggctagg cagatggtcc aggccatgag aaccatcggc      660
acccacccca gcagctctgc tggcctgaag aacgacctgc tggaaaacct gcaggcctac      720
cagaaaagaa tgggcgtcca gatgcagaga ttcaagtga                             759
```

CHARACTERIZATION OF INFLUENZA VACCINES

CROSS REFERENCE TO RELATED APPLICATION

This application is a National Phase application under 35 U.S.C. § 371 of International Application No. PCT/US2016/052802, filed Sep. 21, 2016, which claims priority to U.S. Provisional Application No. 62/221,336, filed Sep. 21, 2015, which is incorporated herein by reference in its entirety.

BACKGROUND

Influenza virus is a member of Orthomyxoviridae family. There are three subtypes of influenza viruses, designated influenza A, influenza B, and influenza C. The influenza virus contains a segmented negative-sense RNA genome, which encodes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2). The HA, NA, M1, and M2 are membrane associated, whereas NP, PB1, PB2, PA, and NS2 are nucleocapsid associated proteins. The HA and NA proteins are envelope glycoproteins, responsible for virus attachment and penetration of the viral particles into the cell, and the sources of the major immunodominant epitopes for virus neutralization and protective immunity. Influenza A viruses are classified into subtypes based on antibody responses to HA and NA. These different types of HA and NA form the basis of the H and N distinctions in, for example, H5N1. There are 16 H and 9 N subtypes known, but only H 1, 2 and 3, and N 1 and 2 are commonly found in humans. Both HA and NA proteins are considered the most important components for prophylactic influenza vaccines.

BRIEF SUMMARY

Provided herein are optimized, recombinant influenza HA polypeptides that elicit immune responses. Also provided are compositions and kits comprising the optimized HA polypeptides as well as methods of making and using the optimized HA polypeptides.

BRIEF DESCRIPTION OF THE DRAWINGS

FIG. 5 is a schematic showing the geometric mean HAI titers and number of strains recognized by elicited antisera against the H3N2 dirft varaint strains (2004-2007).

FIG. 6 is a graph showing the strains with HAI reactivity against a panel of 15 2004-2009 virus variants.

DETAILED DESCRIPTION

Figures 1, 2:
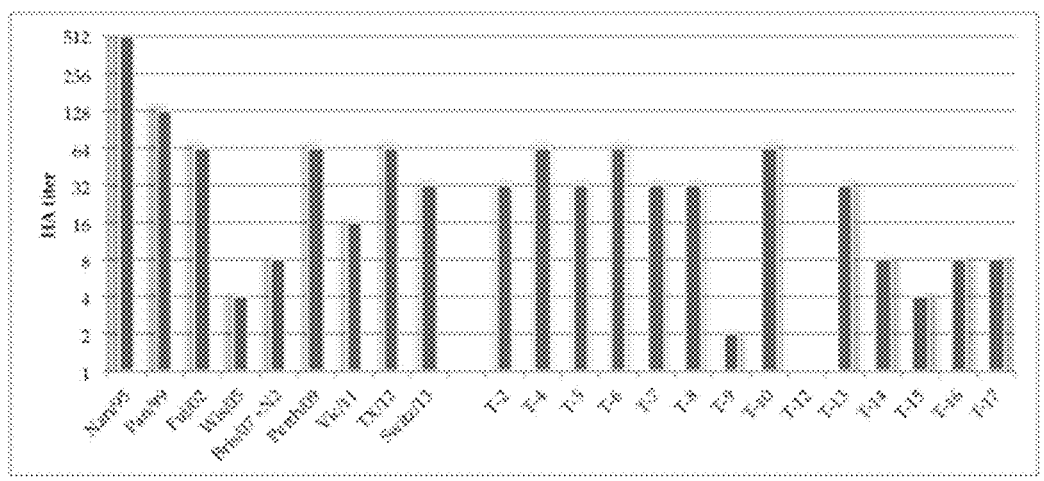
FIG. 1 is a graph showing expression of exemplary optimized HA polypeptides in VLP platform at 72 hours.
FIG. 2 is a schematic of the results of a hemagglutination inhibition (HAI) assay. Following vaccination in mice, serum samples were collected at week 10 post-vaccination and sera was tested in an HAI assay against a panel of wild-type H3N2 influenza viruses. The number of mice (out of 5 mice per group) that reached the 1:40 threshold is listed as the number in the table.

Current vaccination approaches primarily rely on the induction of antibodies recognizing the hemagglutinin (HA) protein. The HA glycoprotein is expressed as a trimeric complex of identical subunits on the surface of influenza virions, and mediates virus attachment and subsequent membrane fusion with target cells (Skehel and Wiley, Annu. Rev. Biochem. 69:531-569 (2000); Bouvier and Palese, Vaccine 12:26, Suppl. 4:D49-53 (2008), which are incorporated by reference herein in their entireties). Individual HA monomers can be further segregated into the membrane distal globular head and membrane proximal stalk domains. The globular head encodes the receptor-binding site (RBS) and the stalk domain encodes the fusion peptide.

Antibodies directed against HA, and more specifically to epitopes in close proximity to the RBS within the globular head region, are elicited following influenza infection or vaccination (Gerhard et al., Nature 290(5808):713-7 (1981); Wilson et al., Virology 458-459:114-24 (2014); Carter, et al., J. Virology, 87(3):1400-10 (2013); Wrammert, et al., Nature, 453(7195):667-71 (2008); Huang, et al., J. Infect. Dis., 209(9):1354-1361 (2014), which are incorporated by reference herein in their entireties). These antibodies possess potent neutralization capacity through their ability to interfere with viral attachment to target cells and are readily detected using the hemagglutinin inhibition (HAI) assay (Skehel and Wiley, Annu. Rev. Biochem. 69:531-569 (2000); Ohmit, et al., J. Infect. Dis. 204(12):1879-85 (2011), which are incorporated by reference herein in their entireties). While antibodies with HAI activity can prevent influenza infection, they are largely strain-specific. Accumulation of point mutations within the globular head region of HA, termed antigenic drift, generates viral escape variants and often evasion of pre-existing immunity (Ohmit, et al., J. Infect. Dis. 204(12):1879-85 (2011); Webster, Nature, 296 (5853):115-21 (1982); Knossow and Skehel, Immunology 119(1):1-7 (2006), which are incorporated by reference herein in their entireties). Moreover, antigenic drift necessitates frequent reformulation of the seasonal vaccine; a process that is both expensive and time-consuming. Therefore, a need exists for development of vaccines that generate broadly cross-reactive neutralizing antibodies. Such vaccines are provided herein.

Hemagglutinin (HA) is an influenza virus surface glycoprotein. HA mediates binding of the virus particle to a host cells and subsequent entry of the virus into the host cell. The nucleotide and amino acid sequences of numerous influenza HA proteins are known in the art and are publically available, such as those deposited with GenBank. HA (along with NA) is one of the two major influenza virus antigenic determinants. Provided herein are computationally optimized broadly reactive antigen (COBRA) HA proteins. Specifically, provided herein are isolated recombinant influenza HA polypeptides comprising at least 95%, 96%, 97%, 98%, or 99% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. Optionally, the isolated recombinant influenza HA polypeptides comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. Optionally, the isolated recombinant influenza HA polypeptides are SEQ ID NO:2, SEQ ID NO:4, SEQ ID NO:5, SEQ ID NO:6, SEQ ID NO:7, SEQ ID NO:8, SEQ ID NO:10, SEQ ID NO:11, or SEQ ID NO:13.

A recombinant nucleic acid, protein or virus is one that has a sequence that is not naturally occurring and/or has a sequence that is made by an artificial combination of two otherwise separated segments of sequence. When used in reference to the optimized influenza HA polypeptides describe herein, for example, the term refers to the fact that the HA polypeptides have been designed (i.e., are not naturally occurring) and/or whose existence and production require one or more actions. The artificial production or combination is often accomplished by chemical synthesis and/or by the artificial manipulation of isolated segments of nucleic acids, for example, by genetic engineering techniques.

As used herein, an "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses, as well as chemically synthesized nucleic acids or peptides.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Also provided herein are isolated nucleic acid molecules comprising nucleotide sequences encoding the provided recombinant, hybrid influenza hemagglutinin (HA) polypeptides. Specifically, provided are isolated recombinant nucleic acid molecules comprising a nucleotide sequence encoding an influenza hemagglutinin (HA) polypeptide, wherein the nucleotide sequence encoding the HA polypeptide is at least at least 95%, 96%, 97%, 98%, or 99% identical to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. Optionally, the nucleic acid sequences comprise SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments, the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein,

*Oligonucleotides and Analogues: A Practical Approach*, Oxford University Press); and peptide nucleic acid backbones and linkages. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

Nucleic acids are linear polymers (chains) of nucleotides, which consist of a purine or pyrimidine nucleobase or base, a pentose sugar, and a phosphate group. As used herein, a "polymer backbone" refers to the chain of pentose sugars and phosphate groups lacking the bases normally present in a nucleic acid.

Nucleic acids can include nonspecific sequences. As used herein, the term "nonspecific sequence" refers to a nucleic acid sequence that contains a series of residues that are not complementary to or are only partially complementary to any other nucleic acid sequence. By way of example, a nonspecific nucleic acid sequence is incapable of hybridizing to any other nucleic acid sequence under hybridizable conditions. Optionally, a nonspecific nucleic acid sequences is a sequence that is not substantially identical to any other nucleic acid sequence. By way of another example, a nonspecific nucleic acid sequence is a sequence of nucleic acid residues that does not function as an inhibitory nucleic acid. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g., mRNA) or altering transcript splicing (e.g. single stranded morpholino oligo).

A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "codon-optimized" nucleic acid refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein.

The terms "identical" or percent sequence "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

Also provided are vectors comprising nucleic acid sequences encoding the provided influenza hemagglutinin (HA) polypeptides. Specifically, provided are isolated vectors comprising SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. Also provided are a plurality of vectors comprising (i) a vector comprising SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26, encoding an HA polypeptide; (ii) a vector comprising a nucleic acid sequence encoding an influenza neuraminidase (NA); and (iii) a vector comprising a nucleic acid sequence encoding an HIV GAG polypeptide. Optionally, provided are a plurality of vectors comprising (i) a vector comprising SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26, encoding an HA polypeptide; (ii) a vector comprising a nucleic acid sequence encoding an influenza neuraminidase (NA); and (iii) a vector comprising a nucleic acid sequence encoding an influenza M1 polypeptide. Optionally, the amino acid sequence of the NA comprises SEQ ID NO:27 and the amino acid sequence of the M1 polypeptide comprises SEQ ID NO:29. Optionally, the nucleic acid sequence encoding the NA polypeptide comprises SEQ ID NO:28 and the nucleic acid sequence encoding the M1 polypeptide comprises SEQ ID NO:30.

As used herein, a matrix (M1) protein refers to the influenza virus structural protein found within the viral envelope. M1 is thought to function in assembly and budding. As used herein, a neuraminidase (NA) refers to the influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants.

As used herein, a vector refers to a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes. In some embodiments of the present disclosure, the vector encodes an influenza HA, NA or M1 protein. Optionally, the vector is the pTR600 expression vector (U.S. Patent Application Publication No. 2002/0106798; Ross et al., *Nat. Immunol.* 1(2):102-103, 2000; Green et al., *Vaccine* 20:242-248, 2001, which are incorporated by reference herein in their entireties).

Construction of suitable vectors containing the nucleic acid sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

The provided vectors can contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Enhancers can be used to function to increase transcription from nearby promoters. Vectors may also contain sequences necessary for the termination of transcription referred to as terminators. The identification and use of terminators in expression vectors is well established. Further, the vectors can include nucleic acid sequence encoding a marker product. This marker product is used to determine if the gene has been delivered to the cell and once delivered is being expressed.

Cells comprising the vectors and nucleic acids are provided. Such cells can be used to generate the provided recombinant, hybrid HA polypeptides and virus-like particles containing the recombinant, hybrid, HA polypeptides. Suitable cells include, but are not limited to, eukaryotic host cells, prokaryotic host cells, and mammalian host cells. For example, the cells can be yeast, insect, avian, plant, *C. elegans*, and mammalian host cells. Examples of mammalian cells include, but are not limited to, COS cells, baby hamster kidney cells, mouse L cells, LNCaP cells, Chinese hamster ovary (CHO) cells, human embryonic kidney (HEK) cells, African green monkey cells, CV1 cells, HeLa cells, MDCK cells, Vero, and Hep-2 cells. Prokaryotic host cells include bacterial cells, for example, *E. coli, B. subtilis*, and mycobacteria.

Provided are methods of making a virus like particle (VLP) comprising culturing the cells comprising the provided nucleic acids or vectors under conditions to produce the VLP and isolating the VLP. Provided is a method of making a VLP comprising transfecting a host cell with a vector encoding a HA polypeptide, a vector encoding an influenza NA polypeptide and a vector encoding an influenza Ml polypeptide under conditions sufficient to allow for expression of the HA, Ml and NA polypeptides and isolating the VLP. Provided is a method of making a VLP comprising transfecting a host cell with a vector encoding an HA polypeptide of, a vector encoding an influenza NA polypeptide and a vector encoding a HIV GAG polypeptide under conditions sufficient to allow for expression of the HA, HIV GAG and NA polypeptides and isolating the VLP. Optionally, the polypeptides comprise a sequence that is at least 95% identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. Optionally, the polypeptides comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. Optionally, the nucleic acid sequences comprise a sequence that is at least 95% identical to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. Optionally, the nucleic acid sequences comprise SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. Optionally, the amino acid sequence of the NA comprises SEQ ID NO:27 and the amino acid sequence of the M1 polypeptide comprises SEQ ID NO:29. Optionally, the nucleic acid sequence encoding the NA polypeptide comprises SEQ ID NO:28 and the nucleic acid sequence encoding the M1 polypeptide comprises SEQ ID NO:30.

The influenza VLPs are made up of the HA, NA and M1 proteins. The production of influenza VLPs has been described in the art and is within the abilities of one of ordinary skill in the art. As described herein, influenza VLPs can be produced by transfection of host cells with plasmids encoding the HA, NA and M1 proteins. After incubation of the transfected cells for an appropriate time to allow for protein expression (such as for approximately 72 hours), VLPs can be isolated from cell culture supernatants. See, for example, U.S. Pat. No. 8,883,171, which is incorporated herein by reference in its entirety. The influenza VLPs disclosed herein can be used as influenza vaccines to elicit a protective immune response against influenza viruses.

Provided are isolated virus-like particles comprising the provided HA polypeptides. Optionally, the virus-like particles comprise an influenza neuraminidase (NA) polypeptide and an influenza matrix (M1) polypeptide. Optionally, the amino acid sequence of the influenza NA polypeptide is at least 95% identical to SEQ ID NO:27, the amino acid sequence of the influenza M1 polypeptide is at least 95% identical to SEQ ID NO:29, or both. Optionally, the virus-like particles comprise an influenza neuraminidase (NA) polypeptide and an HIV GAG polypeptide.

As used herein, virus-like particles (VLP) refer to virus particles made up of one of more viral structural proteins, but lacking the viral genome. Because VLPs lack a viral genome, they are non-infectious. In addition, VLPs can often be produced by heterologous expression and can be easily purified. Most VLPs comprise at least a viral core protein that drives budding and release of particles from a host cell. One example of such a core protein is influenza M1. In some embodiments herein, an influenza VLP comprises the HA, NA and M1 proteins. As described herein, influenza VLPs can be produced by transfection of host cells with plasmids encoding the HA, NA and M1 proteins. After incubation of the transfected cells for an appropriate time to allow for protein expression (such as for approximately 72 hours), VLPs can be isolated from cell culture supernatants. Example 1 provides an exemplary protocol for purifying influenza VLPs from cell supernatants. In this example, VLPs are isolated by low speed centrifugation (to remove cell debris), vacuum filtration and ultracentrifugation through 20% glycerol.

Optionally, recombinant whole influenza viruses comprising the herein provided VIPER HA polypeptides are produced. Recombinant whole influenza viruses can be produced by plasmid-based reverse genetics and cell-based or egg-based technologies. Recombinant viruses containing internal protein genes from a donor virus may be used to prepare inactivated influenza virus vaccines (see, e.g., Fodor, E. et al. *Rescue of influenza A virus from Recombinant DNA*. J. Virol., 1999, 73, 9679-9682; incorporated by reference herein). Recombinant whole influenza viruses can be used to elicit protective immune responses against influenza viruses; for example, they can be administered as components of a live-attenuated or split-inactivated vaccine.

Thus, the immunogenic compositions and vaccines described herein may comprise one of three types of antigen preparation: inactivated whole virus, sub-virions where purified virus particles are disrupted with detergents or other reagents to solubilize the lipid envelope ("split" vaccine) or purified structural influenza polypeptide ("subunit" vaccine). Optionally, virus can be inactivated by treatment with formaldehyde, beta-propiolactone, ether, ether with detergent (such as TWEEN-80®), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., 1998, *Textbook of Influenza*, Blackwell Science, Malden, Mass.; incorporated herein by reference). To assess the potency of the vaccine, the single radial immunodiffusion (SRD) test can be used (Schild et al., 1975, *Bull. World Health Organ.*, 52:43-50 & 223-31; Mostow et al., 1975, *J. Clin. Microbiol.*, 2:531; both of which are incorporated herein by reference).

Optionally, influenza virus for use in vaccines is grown in eggs, for example, in embryonated hen eggs, in which case the harvested material is allantoic fluid. Alternatively or additionally, influenza virus and/or the provided influenza hemagglutinin (HA) polypeptide may be produced from any method using tissue culture to grow the virus. Suitable cell substrates for growing the virus or otherwise recombinantly producing the engineered, structural influenza polypeptides include, for example, CHO cells, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Provided are compositions comprising one or more of the inactivated virus, virus-like particles or one or more of the HA polypeptides. Optionally, the inactivated virus or virus-like particles comprise an HA polypeptide with at least 95%, 96%, 97%, 98%, or 99% identity to a polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14. Optionally, the HA polypeptide comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. Optionally, the compositions comprise a pharmaceutically acceptable excipient or pharmaceutically acceptable carrier. Suitable carriers and their formulations are described in *Remington: The Science and Practice of Pharmacy*, 22nd Edition, Loyd V. Allen et al., editors, Pharmaceutical Press (2012). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Optionally, a pharmaceutical composition can also contain a pharmaceutically acceptable carrier or adjuvant for administration of the vaccine, e.g., the HA polypeptides or VLPs. Optionally, the carrier is pharmaceutically acceptable for use in humans. The carrier or adjuvant should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, ammo acid copolymers and inactive virus particles.

An adjuvant refers to a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207, 646; 6,214,806; 6,218,371; 6,239,116; 6,339,068; 6,406, 705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL. Optionally, the adjuvant is a squalene-based adjuvant. Squalene-based adjuvants are known and include, but are not limited to, MF59 and AS03.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated as tablets, pills, dragees, capsules, liquids, gels, syrups, slurries and suspensions, for ingestion by the patient.

The compositions of the presently disclosed subject matter can further comprise a carrier to facilitate composition preparation and administration. Any suitable delivery vehicle or carrier can be used, including but not limited to a microcapsule, for example a microsphere or a nanosphere (Manome et al. (1994) *Cancer Res* 54:5408-5413; Saltzman & Fung (1997) *Adv Drug Deliv Rev* 26:209-230), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786, 387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al. (1997) Cancer Res 57:1447-1451 and U.S. Pat. Nos. 4,551,482, 5,714,166, 5,510,103, 5,490, 840, and 5,855,900), and a polysome (U.S. Pat. No. 5,922, 545).

Suitable formulations for the provided compositions can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the present disclosure can have a pH between 5.5 and 8.5, between 6 and 8, or about 7. Optionally, the pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

Pharmaceutical compositions can include an effective amount of one or more HA polypeptides and/or VLPs as described herein. Optionally, a pharmaceutical composition can comprise an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and therapeutics or combination of therapeutics selected for administration. The effective amount for a given situation is determined by routine experimentation as practiced by one of ordinary skill in the art.

The pharmaceutical preparation is preferably in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

Provided herein is a method of eliciting an immune response to influenza virus in a subject, comprising administering the influenza HA polypeptide to the subject, wherein the administering elicits an immune response to influenza virus. Optionally, the method further includes administering an adjuvant to the subject. Optionally, the administering comprises administering to the subject a first influenza HA polypeptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. Optionally, the method further includes administering to the subject a second influenza HA polypeptide having an amino acid sequence different from the first influenza HA polypeptide. Optionally, the first and second influenza HA polypeptides are administered simultaneously or concurrently. Optionally, the HA polypeptides are administered as inactivated virus or virus-like particles.

Also provided are methods of immunizing a subject against influenza virus, comprising administering to the subject a composition comprising one or more of the provided HA polypeptides, wherein administration immunizes the subject against influenza virus. Optionally, the HA polypeptides are administered as inactivated virus or virus-like particles. Optionally, the composition further comprises an adjuvant. Optionally, the composition is administered intramuscularly. Optionally, the composition comprises about 1 to about 25 µg of the VLP. Optionally, the composition comprises about 1 to 3 µg of the VLP. Optionally, the composition comprises about 3-15 µg of the VLP.

As used herein, vaccine refers to a preparation of immunogenic material capable of stimulating an immune response, administered for the prevention, amelioration, or treatment of disease, such as an infectious disease. The immunogenic material may include, for example, attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

As used herein, an immune response refers to a response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like. In some embodiments, methods of measuring an immune response include hemagglutination inhibition (HAI) assays to assess functional antibody binding to the HA polypeptides described herein, thereby serving as surrogate measure of influenza vaccine efficacy. HAI assays may use chicken, turkey or horse erythrocytes for the detection of antibodies specific for H3N2. Protective immune responses can be demonstrated by eliciting an average HAI titer of greater than 1:40, which has been correlated with prevention and reduction of influenza illness. HAI antibody titers of approximately 1:32 to 1:40 will generally protect about 50% of subjects from infection after immunization with inactivated human influenza virus vaccine. See, e.g., Treanor, J. and Wright, P. F. Immune correlates of protection against influenza in the human challenge model. Dev. Biol. (Basel), 2003, 115:97-104, which is incorporated by reference herein in its entirety. Optionally, elicitation of a protective immune response can by identified by seroconversion rates. A protective level of seroconversion may be defined as at least a 4-fold rise in HAI titer, for example, a pre-administration or vaccination HAI titer of less than 1:10 and a post vaccinate titer of greater than or equal to 1:40. In other words, successful rates of seroconversion may be defined as the percentage of subjects with either a pre-vaccination HAI titer less than about 1:10 and a post-vaccination HAI titer of greater than about 1:40 or a pre-vaccination HAI titer greater than about 1:10 and a minimum four-fold rise in post-vaccination HAI antibody titer.

As used herein, an immunogen refers to a compound, composition, or substance which is capable, under appropriate conditions, of stimulating an immune response, such as the production of antibodies or a T-cell response in an animal, including compositions that are injected or absorbed into an animal. As used herein, as "immunogenic composition" is a composition comprising an immunogen (such as an HA polypeptide).

As used herein, the term "antigen" refers to a substance that prompts the generation of antibodies and can cause an immune response. It can be used interchangeably in the present disclosure with the term "immunogen". In the strict sense, immunogens are those substances that elicit a response from the immune system, whereas antigens are defined as substances that bind to specific antibodies. An antigen or fragment thereof can be a molecule (i.e., an epitope) that makes contact with a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein).

As used herein, immunize refers to rendering a subject protected from an infectious disease, such as by vaccination.

As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Influenza HA polypeptides and VLPs comprising HA polypeptides, or compositions thereof, can be administered to a subject by any of the routes normally used for introducing recombinant virus into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Influenza VLPs, or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent influenza virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

The pharmaceutical compositions described herein can be administered in a variety of unit dosage forms depending upon the method of administration. Dosages for typical antibody pharmaceutical compositions are well known to those of skill in the art. Such dosages are typically advisory in nature and are adjusted depending on the particular therapeutic context or patient tolerance. The amount antibody adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, Peptides 18: 1431-1439, 1997; Langer, Science 249: 1527-1533, 1990.

"Therapeutically-effective amount" or "an amount effective to reduce or eliminate infection" or "an effective amount" refers to an amount of an antibody composition that is sufficient to prevent influenza virus infection or to alleviate (e.g., mitigate, decrease, reduce) at least one of the symptoms associated with such an infection. It is not necessary that the administration of the composition eliminate the symptoms of influenza virus infection, as long as the benefits of administration of the composition outweigh the detriments. Likewise, the terms "treat" and "treating" in reference to influenza virus infection, as used herein, are not intended to mean that the subject is necessarily cured of infection or that all clinical signs thereof are eliminated, only that some alleviation or improvement in the condition of the subject is effected by administration of the composition.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. In some embodiments, the terms treatment, treat or treating refer to methods of preventing the establishment of, or development of one or more consequences or symptoms associated with, infection by influenza A virus subtype H3N2, including fever, myalgia, headache, malaise, nonproductive cough, sore throat, rhinitis, weight loss, otitis media, nausea, vomiting, and death. For example, the terms treatment, treat, or treating can refer to methods of reducing the effects of one or more consequences or symptoms of infection by influenza A virus subtype H3N2. Thus, the methods of treatment disclosed herein can refer to a 10%, 20%, 30%, 40%, 50%, 60%, 70%, 80%, 90%, or 100% reduction in the severity of one or more consequences or symptoms of infection by influenza A virus subtype H3N2, including fever, myalgia, headache, malaise, nonproductive cough, sore throat, rhinitis, weight loss, otitis media, nausea, vomiting, and death. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination. Optionally, the terms treatment, treat or treating refer to methods of shortening the duration of one or more symptoms of infection by influenza A virus subtype H3N2, including fever, myalgia, headache, malaise, nonproductive cough, sore throat, rhinitis, weight loss, otitis media, nausea, vomiting. In certain embodiments, the duration of symptoms is shortened to less than 2 weeks, to less than 7 days, and/or to less than 3 days.

"Vertebrate," "mammal," "subject," "mammalian subject," or "patient" are used interchangeably and refer to mammals such as human patients and non-human primates, as well as experimental animals such as rabbits, rats, and mice, cows, horses, goats, and other animals. Animals include all vertebrates, e.g., mammals and non-mammals, such as mice, sheep, dogs, cows, avian species, ducks, geese, pigs, chickens, amphibians, and reptiles.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

Also provided are kits comprising the HA polypeptides produced in accordance with the present disclosure which can be used, for instance, for therapeutic applications described above. Optionally, the kit comprises inactivated viruses of VLPs comprising the HA polypeptides. The article of manufacture comprises a container with a label.

Suitable containers include, for example, bottles, vials, and test tubes. The containers can be formed from a variety of materials such as glass or plastic. The container holds a composition which includes an active agent that is effective for therapeutic applications, such as described above. The active agent in the composition can comprise the HA polypeptide or inactivated viruses or VLPs comprising the HA polypeptides. The label on the container indicates that the composition is used for a particular therapy or non-therapeutic application, and can also indicate directions for either in vivo or in vitro use, such as those described above.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLE

Example 1. Design and Characterization of 113 HA COBRA Influenza Vaccines

Antigen construction and synthesis. Influenza A HA nucleotide sequences isolated from human H3N2 infections were downloaded from the NCBI Influenza Virus Resource database (Bao et al., The Journal of Virology, 82(2):596-601 (2008)). Nucleotide sequences were translated into protein sequences using the standard genetic code. Full-length sequences from H3N2 viral infections isolated from human sources between 1968 and 2013 were used in this analysis. For each round of consensus generation, multiple alignment analysis was applied and the consensus sequence was generated using AlignX (Vector NTI). The final amino acid sequence, termed computationally optimized broadly reactive antigen (COBRA), was reverse translated and optimized for expression in mammalian cells, including codon usage and RNA optimization (Genewiz; Washington, D.C., USA). Fourteen H3N2 HA constructs were synthesized and inserted into the pTR600 expression vector, as previously described (Ross, et al., Nat Immunol 1:127-131 (2000)). COBRA HA antigens were designed to represent different antigenic space. Each COBRA HA structure was generated using the 3D-JIGSAW algorithm (Soding, J. Bioinformatics 21:951-960 (2005); and Soding, J., et al., Nucleic acids research 33:W244-248 (2005)) and renderings were performed using MacPyMol. A phylogenetic tree was inferred from hemagglutinin amino acid sequences using the maximum likelihood method and clade/sub-clade groupings were identified using Jalview (Dundee, UK).

In vitro expression. Human embryonic kidney (HEK) 293T cells ($1\times10^6$) were transiently transfected with 3 μg DNA expressing each COBRA or wild-type HA gene cassette. Cells were incubated for 72 hours at 37° C. and then lysed with 1% Triton-X 100 and clarified supernatant harvested following centrifugation. Cell lysates were then electrophoresed on a 10% SDS-PAGE gel and transferred to a PVDF membrane. The blot was probed with pooled mouse antisera from infections with A/Brisbane/57/2007 and A/California/07/2009 viruses. HA-antibody complexes were then detected using goat anti-mouse IgG HRP (Southern Biotech; Birmingham, Ala., USA). HRP activity was detected using chemiluminescent substrate (Pierce Biotechnology; Rockford Ill., USA) and exposed to X-ray film (ThermoFisher; Pittsburgh, Pa., USA).

Functional characterization. To determine receptor-binding characteristics, virus-like particles (VLPs) were produced from transiently transfected with plasmids expressing HIV-1 Gag, (optimized for expression in mammalian cells), NA (A/mallard/Alberta/24/01; H7N3), optimized for expression in mammalian cells) and COBRA HA or HA from wild-type H3N2 strains and incubated for 72 hours at 37° C. (Medigen Inc, Rockville, Md., USA). Supernatants were collected and VLPs were purified via ultracentrifugation (100,000×g through 20% glycerol, weight per volume) for 4 h at 4° C. The pellets were subsequently resuspended in phosphate buffered saline PBS, pH 7.2 and stored at −80° C. until use. Protein concentration was determined by Micro BCATM Protein Assay Reagent Kit (Pierce Biotechnology, Rockford, Ill., USA). COBRA HA VLPs were prepared in various amounts as measured by total HA protein and each individual preparation was two-fold serially diluted in v-bottom microtiter plates. An equal volume of 1% horse erythrocytes (RBC) (Lampire; Biologicals, Pipersville, Pa., USA) in PBS was added to the diluted VLPs and incubated for 60 minutes at room temperature. The HA titer was determined by the reciprocal dilution of the last well which contained agglutinated RBC.

Vaccine Preparation. HEK 293T cells were transiently transfected with plasmids expressing HIV-1 Gag, (optimized for expression in mammalian cells), NA (A/mallard/Alberta/24/01; H7N3), optimized for expression in mammalian cells) and COBRA HA or HA from wild-type H3N2 strains and incubated for 72 hours at 37° C. (Medigen Inc, Rockville, Md., USA). Supernatants were collected and cell debris removed by low speed centrifugation followed by vacuum filtration through a 0.22 μm sterile filter. VLPs were purified via ultracentrifugation (135,000×g through 20% glycerol, weight per volume) for 4 hours at 4° C. The pellets were subsequently resuspended in PBS pH 7.2 and stored in single use aliquots at −80° C. until use. Total protein concentration was determined by Micro BCATM Protein Assay Reagent Kit (Pierce Biotechnology, Rockford, Ill., USA). Hemagglutination capacity was determined through serial dilution of VLPs, adding equal volume 0.8% turkey red blood cells to a V-bottom 96-well plate for a 30 min incubation at room temperature, and the highest dilution of VLP to have full agglutination of RBCs was considered the endpoint HA titer.

Quantification of HA content on 293T HA-NA-Gag VLPs was carried out using a high-affinity, 96-well flat bottom ELISA plate was coated with 5-10 µg of total protein of VLP and serial dilutions of a recombinant H3 antigen (3006_H3_Vc, Protein Sciences, Meriden, Conn.) in ELISA carbonate buffer (50 mM carbonate buffer, pH 9.5). The plate was incubated overnight at 4° C. on a rocker. Plates were then washed with PBS with 0.05% Tween-20 (PBST). Non-specific epitopes were blocked with 1% bovine serum albumin (BSA) in PBST solution for 1 hour at room temperature (RT). Buffer was removed then stalk-specific Group 2 antibody CR8020 (1:4000 dilution in blocking buffer) was added to plate and incubated for 1 hour at 37° C. Plates were washed and probed with goat anti-human IgG horseradish-peroxidase-conjugated secondary antibody (2040-05, Southern Biotech, Birmingham, Ala.) at dilution of 1:4000 for 1 hour at 37° C. Plates were washed then freshly prepared o-phenylenediamine dihydrochloride (OPD) (P8287, Sigma, City, State, USA) substrate in citrate buffer (P4922, Sigma) was added to wells, followed by 1N $H_2SO_4$ stopping reagent. Plates were read at 492 nm absorbance using a microplate reader (Powerwave XS, Biotek, Winooski, Vt.) and background was subtracted from negative wells. Linear regression standard curve analysis was performed using the known concentrations of recombinant standard antigen to estimate HA content in VLP lots. The results are shown in FIG. 1.

HA-specific content was determined by densitometry of reducing SDS-PAGE gels with the HA band identified by western blotting. Purified VLP's or other HA-containing samples and appropriate standards were electrophoresed on a 4-12% Bis-TRIS SDS-PAGE gel in MOPS buffer and transferred to a PVDF membrane (Life Technologies, Grand Island, N.Y.). The blot was probed with mouse monoclonal antibody 15B7 (Immune Technology Corporation, New York, N.Y.) and the HA-antibody complexes were detected by transilluminating fluorescence from a biotinylated goat anti-mouse IgG and the WesternDot™ 625 Western Blot Kit (Life Technologies). A gel run under identical conditions was stained with Sypro Ruby stain (Life Technologies). Gels and blots were imaged and the migration distances of all bands were recorded using a Chemi-Doc XRS+ camera system with QuantityOne software (Bio-Rad, Hercules Calif.). Molecular weights were calculated for all bands relative to MagicMarkXP standards (Life Technologies). The HA band was identified on the Sypro Ruby-stained gel as the one migrating at the same molecular weight for HA as determined from the western blot. Densities of HA bands from recombinant A/Puerto Rico/8/1934 HA standards (Immune Technology Corp.) were used to generate standard curves. The amount of HA in the purified VLP lanes was calculated by interpolation from the data of the standard curve. Experiments were performed in duplicate or triplicate and multiple exposure times were analyzed for all iterations.

Mouse studies. BALB/c mice (*Mus musculus*, females, 6-8 weeks) were purchased from Jackson Laboratories, (Bar Harbor, Me., USA) and housed in microisolator units and allowed free access to food and water and were cared for under USDA guidelines for laboratory animals and all procedures were reviewed and approved by the Institutional Animal Care and Use Committee (IACUC). Mice (16 mice per group) were vaccinated with purified VLPs (3.0 µg) based upon HA content from the densitometry assay or they were vaccinated with the monovalent inactivated split influenza vaccine (IIV), via intramuscular injection at week 0 and then boosted with the same vaccine at the same dose at weeks 4 and 8. In other cases, mice were primed with one VLP vaccine and boosted with a different vaccine. In addition, some mice were administered a cocktail of H3N2 COBRA VLP vaccines (1.5 ug dose of each of the two vaccines). Vaccines at each dose were formulated with AF03, an emulsified squalene-in-water adjuvant (Sanofi-Pasteur, Lyon, France). Final concentration after mixing 1:1 with VLPs is 2.5% squalene. AF03, an alternative squalene emulsion-based vaccine adjuvant prepared by a phase inversion temperature method or phosphate buffered saline alone was used as a mock vaccination. Twenty-eight days after each vaccination, blood was collected from anesthetized mice via the retro-orbital plexus and transferred to a microfuge tube. Tubes were centrifuged and serum samples were removed and frozen at −20±5° C.

Hemagglutination inhibition (HAI) assay. The HAI assay was used to assess functional antibodies to the HA able to inhibit agglutination of turkey erythrocytes. The protocol was adapted from the CDC laboratory-based influenza surveillance manual (Gillim-Ross, L., and K. Subbarao. Clin Microbiol Rev 19:614-636 (2006)). To inactivate non-specific inhibitors, sera were treated with receptor destroying enzyme (RDE; Denka Seiken, Co., Japan) prior to being tested (Bright, et al., Lancet 366:1175-1181 (2005); Bright, et al., Virology 308:270-278 (2003); Bright, et al., JAMA 295:891-894 (2006); Mitchell, et al., Vaccine 21:902-914 (2003); and Ross, et al., Nat Immunol 1:127-131 (2000)). Briefly, three parts RDE was added to one part sera and incubated overnight at 37° C. RDE was inactivated by incubation at 56° C. for approximately 30 minutes. RDE treated sera was two-fold serially diluted in v-bottom microtiter plates. An equal volume of each H3N2 virus, adjusted to approximately 8 HAU/50 µl, was added to each well. The plates were covered and incubated at room temperature for 20 min followed by the addition of 1% turkey erythrocytes (RBC) (Lampire Biologicals, Pipersville, Pa., USA) in PBS. Red blood cells were stored at 4° C. and used within 72 hours of preparation. The plates were mixed by agitation, covered, and the RBCs were allowed to settle for 1 hour at room temperature. The HAI titer was determined by the reciprocal dilution of the last well that contained nonagglutinated RBC. Positive and negative serum controls were included for each plate. All mice were negative (HAI≤1:10) for pre-existing antibodies to currently circulating human influenza viruses prior to vaccination.

Plaque Assay. Madin-Darby Canine Kidney (MDCK) cells were plated ($5 \times 10^5$) in each well of a 6-well plate. Samples were diluted (final dilution factors of 100 to $10^{-6}$) and overlayed onto the cells in 100 µl of DMEM supplemented with penicillin-streptomycin and incubated for 1 hour. Samples were removed, cells were washed twice and media was replaced with 2 ml of L15 medium plus 0.8% agarose (Cambrex; East Rutherford, N.J., USA) and incubated for 72 hours at 37° C. with 5% CO2. Agarose was removed and discarded. Cells were fixed with 10% buffered formalin, and then stained with 1% crystal violet for 15 minutes. Following thorough washing in dH2O to remove excess crystal violet, plates were allowed to dry, plaques counted, and the plaque forming units (PFU)/ml were calculated.

Statistical Analysis. Statistical significance of the antibody data was determined using a two-way analysis of variance (ANOVA) with Bonferroni's post-test to analyze differences between each vaccine group for the different test antigens (multiparametric). Differences in weight loss, sickness score, and viral titers were analyzed by two-way ANOVA, followed by Bonferroni's post-test for each vaccine group at multiple time points. Significance was defined as p<0.05. Statistical analyses were done using GraphPad Prism software.

FIG. 2 is a schematic representation of HAI results in table format. Following vaccination in mice, serum samples were collected at week 10 post-vaccination and sera was tested in an HAI assay against a panel of wild-type H3N2 influenza viruses. Each number represents the number of mice that have a positive HAI titer of 1:40 or greater. The number of mice (out of 5 mice per group) that reached the 1:40 threshold is listed as the number in the table.

Example 2. Analysis and Characterization of H3 HA COBRA Vaccines

Materials and Methods.

Antigen construction and synthesis. Influenza A HA protein sequences from 6,430 human H3N2 infections collected from Jan. 1, 1968-Dec. 15, 2013 were downloaded from the Global Initiative on Sharing Avian Influenza Data (GISAID) database and organized by the year of collection. For each round of consensus generation, multiple sequence alignment was performed using Geneious® MUSCLE alignment method and phylogenetic neighbor-joining trees were constructed, such that trees were rooted to the oldest sequences collected in 1968. Full-length HA sequences were aligned and the most common residue found among a designated set of viruses were used to yield the primary consensus sequence and ambiguities were avoided through alignment of odd-number of sequences. Multiple rounds of consensus assembly were layered to yield secondary, tertiary, and quaternary consensus sequences that were designed to represent different antigenic spaces that overlapped periods of time that wild-type vaccine strains that were recommended from 1968-2013. The final amino acid sequences were then renamed T-series computationally optimized broadly reactive antigen (COBRA). Fifteen H3N2 HA constructs were synthesized and inserted into the pTR600 expression vector, as previously described (Ross et al., Nat. Immunol. 1:127-131 (2000)). COBRA HA antigens were designed to represent different antigenic spaces. For example, constructs T-2 through T-7 were designed to represent non-overlapping periods of time spanning 4-6 years using H3 sequences from human isolates collected between 1980 through 2010, and T-11 was generated using HA sequences isolated from 2011-2013. The COBRA HA constructs, T-9, T-12, T-13, T-14, T-15, T-16, and T-17, represent an antigenic space from 1968-2013 using various multi-consensus layering approaches.

Cartography and predictive structure-homology modeling methods. Human, influenza A (subtype H3N2) hemagglutinin protein sequences were obtained from the NCBI Influenza Virus Resource database, trimmed to remove signal peptides, transmembrane regions, and cytoplasmic tails, and the resulting ectodomain sequences were aligned using MAFFT. The pairwise dissimilarity matrix was calculated from the multiple-sequence alignment based on the Hamming distance between pairs of sequences with no prior assumptions regarding the function or structure of the sequences. Principal component analysis (PCA) was applied to the dissimilarity matrix for the purpose of dimension reduction and to facilitate visualization of the relative distances between HA proteins. The first two or three principal components were retained for visualizing protein relationships in sequence space and represent a reasonable approximation of the general structure of the phylogenetic tree. Calculations were performed using custom scripts written in python and R. Each COBRA HA predictive structure was generated using the SWISS-MODEL algorithm (Kiefer et al., Nucleic Acids Res. 37:D387-392 (2009); Arnold et al., Bioinformatics 22:195-201 (2006); and Biasini et al., Nucleic Acids Res. 42:W252-258 (2014)) implementing the PDB ID 2yp2.1.a, the crystal structure of a human H3N2 2004 virus (Lin et al., PNAS 109:21474-21479 (2012), as the HA template and renderings were performed using MacPyMol. Additional modifications were performed by color-coding of antigenic sites based on literature (Koel et al., Science 342:978-979 (2013); Lewis et al., Journal of Virology 88:4752-4763 (2014); and Stray and Pittman, Virol. J. 9:91 (2012)). Separate frames were collected of the surface-rendered hemagglutinin structures at the matched x-, y-, and z-coordinates.

Vaccine preparation. Mammalian 293T cells were transfected with one of three plasmids expressing either the influenza neuraminidase (A/mallard/Alberta/24/01, H7N3), the HIV p55 Gag sequences and one of the the various H3N2 wild-type or COBRA HA expressing plasmids on previously described mammalian expression vectors (Green et al., Journal of Virology 77:2046-2055 (2003)). Following 72 hours of incubation at 37° C., supernatants from transiently transfected cells were collected, centrifuged to remove cellular debris, and filtered through a 0.22 μm pore membrane. Mammalian virus-like particles (VLPs) were purified and sedimented by ultracentrifugation on a 20% glycerol cushion at 135,000×g for 4 hours at 4° C. VLPs were resuspended in phosphate buffered saline (PBS) and total protein concentration assessed by conventional bicinchoninic acid assay (BCA). Hemagglutination activity of each preparation of VLPs was determined by adding equal volume turkey red blood cells (RBCs) to a V-bottom 96-well plate and incubating with serially diluted volumes of VLPs for a 30 min incubation at RT. The highest dilution of VLP with full agglutination of RBCs was considered the endpoint HA titer.

Determination of HA content. A high-affinity, 96-well flat bottom ELISA plate was coated with 5-10 μg of total protein of VLP and serial dilutions of a recombinant H3 antigen (3006_H3_Vc, Protein Sciences, Meriden, Conn.) in ELISA carbonate buffer (50 mM carbonate buffer, pH 9.5) and plate was incubated overnight at 4° C. on a rocker. The next morning, plates were washed PBS with 0.05% Tween-20 (PBST), then non-specific epitopes were blocked with 1% bovine serum albumin (BSA) in PBST solution for 1 hour at room temperature (RT). Buffer was removed then stalk-specific Group 2 antibody CR8020 was added to plate and incubated for 1 hour at 37° C. Plates were washed and probed with goat anti-human IgG horseradish-peroxidase-conjugated secondary antibody (2040-05, Southern Biotech, Birmingham, Ala.) for 1 hour at 37° C. Plates were washed then freshly prepared o-phenylenediamine dihydrochloride (OPD) (P8287, Sigma, City, State, USA) substrate in citrate buffer (P4922, Sigma, St. Louis, Mo.) was added to wells, followed by 1N H2SO4 stopping reagent. Plates were read at 492 nm absorbance using a microplate reader (Powerwave XS, Biotek, Winooski, Vt.) and background was subtracted from negative wells. Linear regression standard curve analysis was performed using the known concentrations of recombinant standard antigen to estimate HA content in VLP lots.

Mouse studies. BALB/c mice (*Mus musculus*, females, 6 to 8 weeks old) were purchased from Jackson Laboratory (Bar Harbor, Me., USA) and housed in microisolator units and allowed free access to food and water and were cared for under USDA guidelines for laboratory animals. All procedures were reviewed and approved by the Institutional Animal Care and Use Committee (IACUC). Mice (5 mice per group) were vaccinated with purified VLPs (3.0 µg/mouse) based upon HA content from the ELISA quantification and vaccines were delivered via intramuscular injection at week 0 and then boosted with the same vaccine at the same dose at weeks 4 and 8. In other cases, mice were primed with one VLP vaccine and boosted with a different vaccine. In addition, some mice were administered a cocktail of H3 COBRA VLP vaccines (1.5-µg dose of each of the two vaccines) or phosphate-buffered saline alone as a mock vaccination. Vaccines at each dose were formulated with an emulsified squalene-in-water adjuvant (Sanofi Pasteur, Lyon, France). The final concentration after mixing 1:1 with VLPs is 2.5% squalene. Twenty-eight days after each vaccination, blood samples were collected via the submandibular cheek and transferred to a microcentrifuge tube. The tubes were centrifuged, and serum samples were removed and frozen at −20° C.±5° C.

HAI assay. The hemagglutination inhibition (HAI) assay was used to assess functional antibodies to the HA able to inhibit agglutination of guinea pig and as well as turkey erythrocytes. The protocols were adapted from the WHO laboratory influenza surveillance manual (Organization, W. H. & Network, W. G. I. S. Manual for the Laboratory Diagnosis and Virological Surveillance of Influenza. (World Health Organization, 2011)) and uses the host-species that is frequently used to characterize contemporary H3N2 strains that have preferential binding to alpha (2,6) linked sialic acid receptors (Katz, et al., Expert Rev. Anti. Infect. Ther. 9:669-683 (2011); Oh et al., Journal of Clinical Microbiology 46:2189-2194 (2008)). It was also compared with turkey erythrocytes to compare whether there was a differential in HAI depending on erythrocyte used. To inactivate nonspecific inhibitors, sera were treated with receptor-destroying enzyme (RDE) (Denka Seiken, Co., Japan) prior to being tested. Briefly, three parts of RDE was added to one part of sera and incubated overnight at 37° C. RDE was inactivated by incubation at 56° C. for ~30 min. RDE-treated sera were diluted in a series of twofold serial dilutions in in v-bottom microtiter plates. An equal volume of each H3N2 virus, adjusted to approximately 8 hemagglutination units (HAU)/50 µl, was added to each well. The plates were covered and incubated at room temperature for 20 min, and then 0.8% guinea pig erythrocytes (Lampire Biologicals, Pipersville, Pa., USA) in PBS were added. Red blood cells were stored at 4° C. and used within 72 hours of preparation. The plates were mixed by agitation and covered, and the RBCs were allowed to settle for 1 hour at room temperature. The HAI titer was determined by the reciprocal dilution of the last well that contained nonagglutinated RBCs. Positive and negative serum controls were included for each plate. All mice were negative (HAI≤1:10) for preexisting antibodies to currently circulating human influenza viruses prior to vaccination and seroprotection was defined as HAI titer>1:40 and seroconversion as a 4-fold increase in titer compared to baseline, as per the WHO and European Committee for Medicinal Products to evaluate influenza vaccines (Agency, E. M. in EMA/CHMP/VWP/457259/2014 (ed Committee for Medicinal Products for Human Use) (London E14 4HB, UK, 2014)); however, often examined was a more stringent threshold of >1:80. Mice are naïve and seronegative at the time of vaccination, thus seroconversion and seroprotection rates are interchangeable in this study.

Viruses. H3N2 viruses were obtained through the Influenza Reagents Resource (IRR), BEI Resources, the Centers for Disease Control (CDC), or provided by Sanofi-Pasteur. Viruses were passaged once in the same growth conditions as they were received, in either embryonated chicken eggs or semi-confluent Madin-Darby canine kidney (MDCK) cell culture as per the instructions provided the WHO9. Virus lots were tittered with both guinea pig and turkey erythrocytes and made into aliquots for single-use applications. The H3N2 vaccine panel includes the following strains: A/Hong Kong/1/1968 (NR-28620), A/Port Chalmers/1/1973, A/Mississippi/1/1985×PR/8 (NR-3502), A/Sichuan/60/1989×PR/8 (NR-3492), A/Nanching/933/1995, A/Sydney/05/1997, A/Panama/2007/1999, A/Fujian/411/2002, A/New York/55/2004 (FR-462), A/Wisconsin/67/2005 (FR-397), A/Brisbane/10/2007, A/Perth/16/2009, A/Victoria/361/2011, A/Texas/50/2012, and A/Switzerland/9715293/2013 (J1506B), A/Hong Kong/4801/2014. All viruses were characterized for ability to agglutinate turkey and guinea pig erythrocytes.

Figures 3, 4:
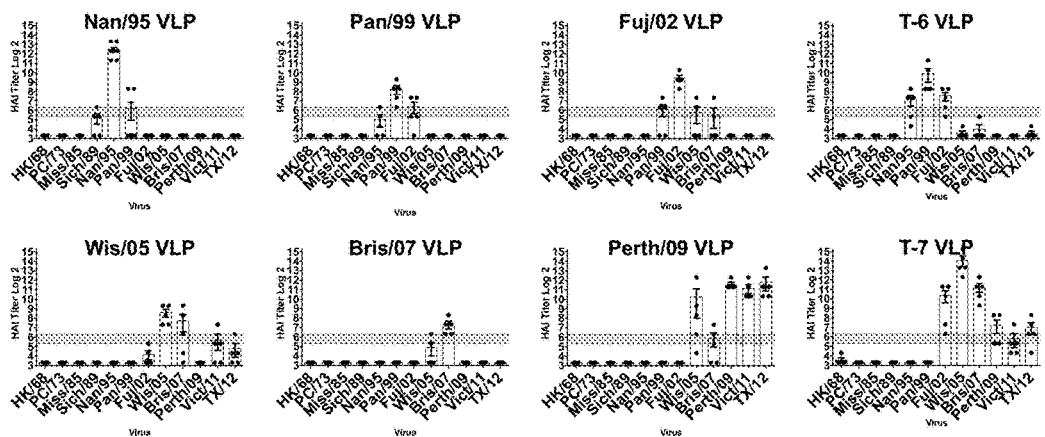
FIG. 3 are graphs showing HAI titers elicited by wild-type H3 HA VLP vaccines and T-6 and T-7 COBRA vaccines.
FIG. 4 is a schematic showing the geometric mean HAI titers and number of strains recognized by elicited antisera against the 10 historical wild-type H3N2 strains.

The Results are shown in FIGS. 3-6. FIG. 3 are graphs showing H3 COBRA vaccines have enhanced reactivity to H3N2 vaccine panel. T-6 COBRA elicits reactivity to all three Nan/95, Pan/99 and Fuj/02 while no wild type (WT) virus cross reacts against all three with greater seroconversion. T-7 COBRA elicits reactivity to Wis/05, Bris/07 and Perth/09 while WT vaccines lose cross reactivity to each other. FIG. 4 is a schematic showing the H3 COBRA elicited antisera react against more antigenically diverse antigens by HAI than conventional strains. FIG. 5 is a schematic showing cross reactivity of T-6, T-7, T-8, T-10 and T-11 COBRA vaccines. FIG. 6 is a graph showing the strains with HAI reactivity against a panel of 15 2004-2009 virus variants.

As described herein, unique H3 COBRA constructs can be designed against antigenic spaces by time. The wild type (WT) and COBRA HA expressing VLPs were tested in mice and the data collectively shows the H3 COBRA vaccines have enhanced reactivity. Specifically, H3 COBRA VLPs elicited antisera reacts against more antigenically diverse H3N2 stains as determined by HAI than WT VLPs. Further, broad HAI breadth was obtained using heterologous prime-boost immunization. Finally, T-7 elicited superior HAI reactivity and T-8 and T-11 elicited high reactivity to a panel of 15 2004-2009 variants as compared to the WT vaccines.

What is claimed is:

1. A recombinant influenza HA polypeptide comprising SEQ ID NO:1, SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, or SEQ ID NO:12.

2. The recombinant influenza HA polypeptide of claim 1, wherein the recombinant influenza HA polypeptide comprises SEQ ID NO:2, SEQ ID NO:4, SEQ ID NO:5, SEQ ID NO:6, SEQ ID NO:8, SEQ ID NO:10, or SEQ ID NO:11.

3. A composition comprising the influenza HA polypeptide of claim 1.

4. A virus-like particle comprising the polypeptide of claim 1.

5. The virus-like particle of claim 4, further comprising an influenza neuraminidase (NA) polypeptide and an influenza matrix (M1) polypeptide.

6. The virus-like particle of claim 5, wherein the amino acid sequence of the influenza NA polypeptide is at least 95% identical to SEQ ID NO:27, the amino acid sequence of the influenza M1 polypeptide is at least 95% identical to SEQ ID NO:29, or both.

7. The virus-like particle of claim 6, further comprising an influenza neuraminidase (NA) polypeptide and an HIV GAG polypeptide.

8. A composition comprising the virus-like particles of claim 4, and a pharmaceutically acceptable excipient.

9. A recombinant nucleic acid molecule comprising a nucleotide sequence encoding an influenza hemagglutinin (HA) polypeptide, wherein the nucleotide sequence encoding the HA polypeptide is at least at least 95% identical to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26.

10. The recombinant nucleic acid molecule of claim 9, wherein the nucleotide sequence encoding the HA polypeptide comprises SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26.

11. A vector comprising one or more of the nucleic acid sequences of claim 9.

12. A vector comprising SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26.

13. A plurality of vectors comprising
(i) a vector comprising SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26, encoding an HA polypeptide;
(ii) a vector comprising a nucleic acid sequence encoding an influenza neuraminidase (NA); and
(iii) a vector comprising a nucleic acid sequence encoding an HIV GAG polypeptide.

14. A plurality of vectors comprising
(i) a vector comprising SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26, encoding an HA polypeptide;
(ii) a vector comprising a nucleic acid sequence encoding an influenza neuraminidase (NA); and
(iii) a vector comprising a nucleic acid sequence encoding an influenza M1 polypeptide.

15. An isolated cell comprising the vector of claim 11.

* * * * *